United States Patent [19]
Eyre

[11] Patent Number: 6,100,379
[45] Date of Patent: *Aug. 8, 2000

[54] SYNTHETIC PEPTIDES CORRESPONDING TO TELOPEPTIDE SEQUENCES OF CROSS-LINKED TYPE II COLLAGEN METABOLITES

[75] Inventor: David R. Eyre, Mercer Island, Wash.

[73] Assignee: Washington Research Foundation, Seattle, Wash.

[ * ] Notice: This patent is subject to a terminal disclaimer.

[21] Appl. No.: 09/347,503

[22] Filed: Jul. 2, 1999

Related U.S. Application Data

[63] Continuation of application No. 09/237,176, Jan. 25, 1999, Pat. No. 6,048,705, which is a continuation of application No. 09/047,144, Mar. 24, 1998, Pat. No. 5,962,639, which is a continuation of application No. 08/803,960, Feb. 21, 1997, abandoned, which is a continuation of application No. 08/664,102, Jun. 13, 1996, Pat. No. 5,677,198, which is a continuation of application No. 08/567,618, Dec. 4, 1995, Pat. No. 5,656,439, which is a continuation of application No. 08/457,831, Jun. 1, 1995, Pat. No. 5,576,189, which is a continuation of application No. 08/221,705, Apr. 1, 1994, Pat. No. 5,473,052, which is a continuation of application No. 07/614,719, Nov. 21, 1990, Pat. No. 5,300,434, which is a continuation-in-part of application No. 07/444,881, Dec. 1, 1989, Pat. No. 5,140,103, which is a continuation-in-part of application No. 07/118,234, Nov. 6, 1987, Pat. No. 4,973,666.

[51] Int. Cl.⁷ ...................................................... A61K 38/04
[52] U.S. Cl. .......................... 530/326; 530/350; 530/332; 530/356
[58] Field of Search ..................................... 530/350, 356, 530/323–330, 332

[56] References Cited

U.S. PATENT DOCUMENTS

| | | |
|---|---|---|
| 3,600,132 | 8/1971 | Goverde . |
| 4,094,646 | 6/1978 | Stern et al. . |
| 4,298,593 | 11/1981 | Ling . |
| 4,312,853 | 1/1982 | Timpl . |
| 4,371,374 | 2/1983 | Cerami et al. . |
| 4,504,587 | 3/1985 | Timpl et al. . |
| 4,731,326 | 3/1988 | Thompson et al. . |
| 4,774,227 | 9/1988 | Piez et al. . |
| 5,140,103 | 8/1992 | Eyre ........................................ 530/327 |
| 5,300,434 | 4/1994 | Eyre . |
| 5,320,970 | 6/1994 | Eyre . |
| 5,455,179 | 10/1995 | Eyre . |
| 5,472,884 | 12/1995 | Eyre . |
| 5,532,169 | 7/1996 | Eyre ........................................ 436/518 |

FOREIGN PATENT DOCUMENTS

| | | |
|---|---|---|
| 128 041 | 6/1983 | European Pat. Off. . |
| 289 314 | 4/1988 | European Pat. Off. . |
| 505210 A2 | 9/1992 | European Pat. Off. . |
| 424428 B1 | 9/1994 | European Pat. Off. . |
| 394296 B1 | 1/1995 | European Pat. Off. . |
| 502928 B1 | 1/1996 | European Pat. Off. . |
| 2205643 | 12/1988 | United Kingdom . |
| WO 88/08980 | 11/1988 | WIPO . |
| WO 89/04491 | 5/1989 | WIPO . |
| WO 89/12824 | 12/1989 | WIPO . |
| WO 90/04417 | 5/1990 | WIPO . |
| WO 90/08195 | 7/1990 | WIPO . |
| WO 91/08478 | 6/1991 | WIPO . |
| WO 92/21698 | 12/1992 | WIPO . |
| WO 95/08115 | 3/1995 | WIPO . |
| WO 96/12193 | 4/1996 | WIPO . |

OTHER PUBLICATIONS

U.S. application No. 07/432,044, Termine, filed Nov. 1989.
Black, et al., "Urinary excretion of the hydroxypyridinium cross links of collagen in patients with rheumatoid arthritis", *Annals of the Rheumatic Diseases*, 48:641–644 (1989).

(List continued on next page.)

*Primary Examiner*—Jeffrey Stucker
*Attorney, Agent, or Firm*—Christensen O'Connor Johnson & Kindness PLLC

[57] ABSTRACT

Peptides synthesized to match the human α1(II) carboxy-telopeptide sequences of type II collagen degradation products in body fluids, preferably Glu-Lys-Gly-Pro-Asp-Pro (SEQ ID NO:6). Useful as calibrators and antigens in immunoassays for detecting type II collagen degradation products in body fluids.

5 Claims, 11 Drawing Sheets

OTHER PUBLICATIONS

Seibel, et al., "Urinary Hydroxy–pyridinium Crosslinks Provide Indices of Cartilage and Bone Involvement in Arthritic Diseases", *the Journal of Rheumatology*, 16:964–970 (1989).

Baldwin, et al., "Structure of cDNA clones coding for human type II procollagen: the al (II) chain is more similar to the al(I) chain than two other a chains of fibrillar collagens", *Biochemistry Journal*, 262:521–528 (1989).

Ala–Kokko, et al., "Structure of cDNA clones coding for the entire preproal (III) chain of human type III procollagen: Differences in protein structure from type I procollagen and conservation of codon preferences," *Biochemistry Journal*, 260:509–516 (1989).

Seibel, "Komponenten der extrazllularen Gewebematrix als potentielle 'Marker' des Bindegewebs–, Knorpel–und Knochenmetabolismus bei Erkrankungen des Bewegungsapparates", *Zeitschrift fur Rheumatologie*, 48:6–18 (1989).

Dodge and Poole, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1," Journal of Clinical Investigation, 83:647–661 (1989).

Niemela, "Radioimmunoassays for Type III Procollagen Amino–Terminal Peptides in Humans," *Clinical Chemistry*, 31:1301–1304 (1985).

Sangiorgi, et al., "Isolation and Partial Characterization of the entire human proal (II) collagen gene," Nucleic Acids Research, 13:2207–2225 (1985).

Loidl, et al., "Molecular cloning and carboxyl–propeptide analysis of human type III procollagen," *Nucleic Acids Research*, 12:9383–9394 (1984).

Wu and Eyre, "Identification of Hydroxypyridinium Cross–Linking Sites in Type II Collagen of Bovine Articular Cartilage," *Biochemistry*, 23:1850–1857 (1984).

Pierard, et al., "Radioimmunoassay for the Amino–Terminal Sequences of Type III Procollagen in Human Body Fluids Measuring Fragmented Precursor Sequences," *Analytical Biochemistry*, 141:127–136 (1984).

Rohde, et al., "Radioimmunoassay for type III procollagen peptide and its application to human liver disease," *European Journal of Clinical Investigation*, 9:451–459 (1979).

Russell, R.G.G., et al., "Biochemical Markers of Bone Turnover in Paget's Disease," *Metab. Bone Dis. & rel. Res.*, 4 & 5:255–262 (1981).

Drinkwater, B.L., et al., "Bone Mineral Density After Resumption of Menses in Amenorrheic Athletes," JAMA, 256:380–382 (1986).

Drinkwater, B.L., et al., "Bone Mineral Content of Amenorrheic and Eumenorrheic Athletes," *the New England Journal of Medicine*, 311:5;277–281 (1984).

Fujimoto, D., "Evidence for Natural Existence of Pyridinoline Crosslink in Collagen," *Biochemical and Biophysical Research Communications*, 93:948–953 (1980).

Yamauchi, M. et al., "A Comparative Study of the Distribution of the Stable Crosslink, Pyridinoline, in Bone Collagens from Normal, Osteoblastoma, and Vitamin D–Deficient Chicks," *Biochemical and Biophysical Research Communications*, 102:59–65 (1981).

Kuboki, Y., et al., "Location of the Intermolecular Crosslinks in Bovine Dentin Collagen, Solubilization with Trypsin and Isolation of Cross–Link Peptides Containing Dihydroxylysinonorleucine and Pyridinoline," *Biochemical and Biophysical Research Communications*, 102:119–126 (1981).

Gunja–Smith, Z. and Boucek, R.J., "Collagen cross–linking compounds in human urine," *Biochemical Journal*, 197:759–762 (1981).

Tsuchikura, O., et al., "Pyridinoline Fluorescence in Cyanogen Bromide Peptides of Collagen," *Biochemical and Biophysical Research Communications*, 102: 1203–1208 (1981).

Tsuda, M., et al., "Pyridinoline is a Real Moiety of Collagen," *Biochemical and Biophysical Research Communications*, 104:1407–1412 (1982).

Robins, S.P., "An enzyme–linked immunoassay for the collagen cross–link pyridinoline," *Biochemical Journal*, 207:617–620 (1982).

Banes, A.J., et al., "Nonmineralized and Mineralized Compartments of Bone: the Role of Pyridinoline in Nonmineralized Collagen," *Biochemical and Biophysical Research Communications*, 113:975–981 (1983).

Fujimoto, D., et al., "Analysis of Pyridinoline, a Cross–Linking Compound of Collagen Fibers, in Human Urine," *J. Biochem.*, 94:1133–1136 (1983).

Eyre, D.R., et al., "Cross–Linking in Collagen and Elastin," *Ann. Rev. Biochem.*, 53:717–748 (1984).

Light, N. and Bailey, A.J., "Collagen crosslinks: Location of pyridinoline in type I collagen," FEBS 2409, 182:503–508 (1985).

Wu, J–J. and Eyre, D.R., "Fine Powdering Exposes the Mineral–Protected Collagen of Bone to Protease Digestion," *Calcif. Tissue Int.*, 42:243–247 (1988).

Fujimoto, D., et al., "Pyridinoline, A Non–Reducible Crosslink of Collagen. Quantitative Determination, Distribution, and Isolation of a Crosslinked Peptide," *Chemical Abstracts* 89(11):148, (Sep. 11, 1978).

Black, D., et al., "Quantitative Analysis of the Pyridinium Crosslinks of Collagen in Urine Using Ion–Paired Reversed–Phase High–Performance Liquid Chromatography," *Chemical Abstracts* 108(21):354, (May 23, 1988).

Fujimoto, D., et al., "Analysis of Pyridinoline, A Cross–Linking Compound of Collagen Fibers, in Human Urine," *Chemical Abstracts* 99(19): 446–447, (Nov. 7, 1983).

Macek, J., et al., "Determination of Collagen Degradation Products in Human Urine in Osteoarthrosis," *Chemical Abstracts* 108(3):299, (Jan. 18, 1988).

Eyre, D.R., et al., "Quantitation of Hydroxypyridinium Crosslinks in Collagen by High–Performance Liquid Chromatography," *Analytical Biochemistry*, 137:380–388 (1984).

Robins, S.R., et al., "Measurement of the cross linking compound, pyridinoline, in urine as an index of collagen degradation in joint disease," *Annals of the Rheumatic Diseases*, 45:969–973 (1986).

Bernard, M.P., et al., "Nucleotide Sequences of Complementary Deoxyribonucleic Acids for the Proal Chain of Human Type I Procollagen. Statistical Evaluation of Structures that are Conserved During Evolution," *Biochemistry*, 22:5213–5223 (1983).

Goldstein, D., et al., "Simultaneous Measurement of DOPA, DOPAC, and Catecholamines in Plasma by Liquid Chromatography with Electrochemical Detection," *ESA Review*, vol. II, No. 1, pp. 2–11 (1986).

Chu, M–L., et al., "Human proal (I) collagen gene structure reveals evolutionary conservation of a pattern of introns and exons," *Nature* 310(26):337–340 (1984).

Robins, S.P., et al., "Measurement of Hydroxypyridinium Crosslinks of Collagen as an Index of Bone Matrix Degradation," *An Abstract of a Paper*, Lake Garda, Italy (1987).

Kang, A.H. and Gross, J., "Amino Acid Sequence of Cyanogen Bromide Peptides from the Amino–Terminal Region of Chick Skin Collagen," *Biochemistry* 9:796–804 (1970).

Highberger, J.H., et al., "The Amino Acid Sequence of Chick Skin Collagen al–CB7," *Biochemistry* 14(13):2872–2881 (1975).

Fietzek, P.P. and Kuhn, K., "The Covalent Structure of Collagen: Amino Acid Sequence of the N–Terminal Region of a2–CB5 from Rat Skin Collagen," *FEBS Letters* 36(3):289–291 (1973).

Dixit, S.N., et al., "Covalent Structure of Collagen: Amino Acid Sequence of a2–CB5 of Chick Skin Collagen Containing the Animal Collagenase Cleavage Site," *Biochemistry*, 18:3416–3422 (1979).

Dakkak, et al., "Modifications de l'hydroxprolinurie peptidique au cours de la maladie de paget et des ostéomes," *Ann. Biol. Clin.* 37:195–200 (1979).

Teitsson, et al., "Urinary excretion of pyridinium metabolites in a patient with Paget's Disease: new markers for collagen break–down," Abstracts, Scottish Society for Experimental Medicine, May 13, 1988.

Eyre, et al., "Collagen cross–linking in human bone and articular cartilage: Age–related changes in the content of mature hydroxypyridinium residues," *Biochem. J.* 252:495–500 (1988).

Whittle, et al., "Biochemical investigation of possible lesions in human aorta that predispose to dissecting aneurysms: pyridinoline crosslinks," *Cardiovascular Research* 21:161–168 (1987).

Gunja–Smith, Z., "An Enzyme–Linked Immunosorbent Assay to Quantitate the Elastin Crosslink Desmosine in Tissue and Urine Samples," *Analytical Biochemistry* 147:258–264 (1985).

Schuppan, et al., "Radioimmunoassay for the Carboxy–terminal Cross–linking Domain of Type IV (Basement Membrane) Procollagen in Body Fluids," *J. Clin. Invest.* 78:241–248 (Jul. 1986).

Eyre, D.,"Collagen Cross–Linking Amino Acids," In: *Methods in Enzymology*, vol. 144, pp. 115–139, Academic Press, Inc., 1987.

Eyre, et al., "Identification of Urinary peptides derived from cross–linking sites in bone collagen in Paget's Disease," *Journal of Bone and Mineral Research*, 3, Supp. 1 (Jun. 1988).

Eyre, et al., "Reducible Crosslinks in Hydroxylysine–Deficient Collagens of a Heritable Disorder of Connective Tissue," *Proc. Nat. Acad. Sci. USA* 69(9):2594–2598 (Sep. 1972).

Eyre, et al., "Evidence for a previously undetected sequence at the carboxyterminus of the a1 chain of chicken bone collagen," *Biochemical and Biophysical Research Communications* 48(3):720–726 (1972).

Eyre, et al., "The distribution of crosslinking aldehydes in a1 and a2 chains of chicken bone collagen," *Biochimica et Biophysica Acta* 278:206–210 (1972).

Eyre, et al., "Evidence for intramolecular crosslinks in chicken bone collagen: the isolation of peptides containing allysine aldol," *Biochimica et Biophysica Acta* 295:301–307 (1973).

Eyre, et al., "Analysis of aq crosslinked peptide from calf bone collagen: evidence that hydroxylysyl glycoside participates in the crosslinks," *Biochemical and Biophysical Research Communications* 52(2):663–671 (1973).

Eyre, et al., "Isolation of crosslinked peptides from collagen of chicken bone," *Biochem J.* 135:393–403 (1973).

Eyre, et al., "The Hydroxypyridinium crosslinks of skeletal collagens: their measurement, properties and a proposed pathway of formation," *Biochemical and Biophysical Research Communications* 92(2):403–410 (1980).

Walters, et al., "Collagen Crosslinks in Human Dentin: Increasing Content of Hydroxypyridinium Residues with Age," *Calcif. Tissue Int.* 35:401–405 (1983).

Wu, et al., "Identification of Hydroxpyridinium Cross–Linking Sites in Type II Collagen of Bovine Articular Cartilage," *Biochemistry* 23:1850–1857 (1984).

Wu, et al., "Cartilage type IX collagen is cross–linked by hydroxypyridinium residues," *Biochemical and Biophysical Research Communications* 123(3):1033–1039 (1984).

Eyre, et al., "Collagen type IX: evidence for covalent linkages to type II collagen in cartilage," *FEB* 220(2):337–341 (1987).

Beardsworth, et al., "Changes with Age in the Urinary Excretion of Lysyl–and Hydroxylysylpyridinoline, Two New Markers of Bone Collagen Turnover," *Journal of Bone and Mineral Research* 5(7):671–676 (1990).

Eyre, D.R., "Collagen: Molecular Diversity in the Body's Protein Scaffold," *Science* 207:1315–1322 (1980).

Eyre, D.R., "Collagen Stability Through Covalent Crosslinking," In: Pearsons, et al., eds. *Advances in Meat Research, vol. 4, Collagen as a Food.* New York: Van Nostrand Reinhold, 1987.

Eyre, D.R., "Crosslink maturation in bone collagen," In: Veis, A., ed. the *Chemistry and Biology of Mineralized Connective Tissues*, Elsevier North Holland, Inc., 1981.

Eyre, D.R., "Collagen cross–linking," In: Akeson, W.H. et al., eds., AAOS: *Symposium on Heritable Disorders of Connective Tissue*, St. Louis: C.V. Mosby, 1982, pp. 43–58.

Eyre, et al., "Studies on the molecular diversity and cross–linking of Cartilage collagen," In: Peyron, J. G., ed. *Osteoarthritis: Current Clinical and Fundamental Problems*, Paris, France: CIBA–GEIGY, 1984, pp. 117–122.

Delmas, Pierre D., "Biochemical Markers of Bone Turnover for the Clinical assessment of Metabolic Bone Disease," *Endocrinology and Metabolism Clinics of North America*, 19(1) (Mar. 1990).

Uebelhart, et al. "Urinary excretion of pyridinium crosslinks: a new marker of bone resorption in metabolic bone disease" *Bone and Mineral*, 8:87–96 (1990).

Uebelhart, et al. "Effect of Menopause and Hormone Replacement Therapy on the Urinary Excretion of Pyridinium Cross–Links," *Journal of Clinical Endocrinology and Metabolism*, 72(2):367–373 (1991).

Black, D., Duncan, A. and Robins, S.P., "Quantitative analysis of the Pyridinium Crosslinks of Collagen in Urine Using Ion–Paired Reversed–Phase High –Performance Liquid Chromatography," *Analytical Biochemistry* 169:197–203 (1988).

Davison, et al., "The Effects of Acetic Acid on Collagen Cross–Link," *Connective Tissue Research* 1:205–216 (1972).

Fujimoto and Moriguchi, "Pyridinoline, a non–reducible crosslink of collagen ", *J. Biochem.*, 83:863–867 (1978).

Macek and Adam, "Determination of collagen degradation products in human urine in osteoarthrosis," *Z. Rheumatol.* 46:237–240 (1987).

Eyre, D.R., "Evidence for intramolecular cross–links in chicken bone collagen: Isolation of peptides containing allysine aldol," *Chem. Abstracts*, 78(13):81202c (1973).

Kühn, Klaus, "Chemical Properties of Collagen," In: *Immunochemistry of the Extracellular Matrix*, vol. I, pp. 1–29, CRC Press, Inc., 1982.

Robins, "Cross–linking of collagen", *Biochem. J.* 215:167–173 (1983).

Robins and Duncan, "Pyridinium crosslinks of bone collagen and their location in peptides isolated from rat femur", *Biochem. et Biophys. Acta* 914:233–239 (1987).

Henkel, Werner, Glanville, Robert W., and Oreifendorf, Dieter, "Characterisation of a type–I collagen trimeric cross–linked peptide from calf aorta and its cross–linked structure," *Eur. J. Biochem* 165:427–436, 1987.

Kuivaniemi, et al., "Structure of a full–length cDNA clone for a preproα(I) chain of human type I procollagen," *Biochem. J.* 252:633–640 (1987).

Hanson, D.A., et al., "A specific immunoassay for monitoring human bone resorption: Quantitation of type I collagen cross–linked N–telopeptides in urine," *Journal of Bone & Mineral Research* 7(11): 1251–1258 (1992).

Bernard, M.P. et al., Nucleotide sequences of complementary deoxyribonucleic acids for the $proa_1$ Chain of human type I procollagen; statistical evaluation of structures that are conserved during evolution, *Biochemistry* 22:5213–5223 (1983).

Del Pozo, A.M., et al., "Binding of 1–Anilinonsphthalene–8–Sulfonic Acid to Type I Collagen," *Int. J. Peptide Protein Res.* 28:329–358 (1983).

Robins, S.P., Analysis of the Crosslinking Components in Collagen and Elastin, *Methods of Biochemical Analysis* 28:329–379 (1982).

Fujimoto, D., Isolation and Characterization of a Fluorescent Material in Bovine Achilles Tendon Collagen, *Biochemical and Biophysical Research Communications* 76(4):1124–1129 (1977).

Seibel, et al., "Urinary Hydroxy–pyridinium Crosslinks Provide Indices of Cartilage and Bone Involvement in Arthritic Diseases," *The Journal of Rheumatalogy*, 16(7):964–970 (1989).

Click and Bornstein, Isolation and Characterization of the Cyanogen Bromide Peptides from the α1 and α2 Chains of Human Skin Collagen, *Biochemistry* 9(24):4699–4706 (1970).

Krüger–Franke, M., et al., "Pyridinolinhaltige Kollagenbruchstücke im Urin bei Coxarthrose," *Z. Rheumatol.* 50:323–327 (1991).

Dickson et al., Analysis of the promoter region and the N–propeptide domain of the human proα2(I) collagen gene, *Nucleic Acids Research* 13(10):3427–3438 (1985).

Abbiati et al., Monitoring of free and total urinary pyridinoline and deoxypyridinoline in healthy volunteers: sample relationships between 24–h and fasting early morning urine concentrations, *Bone and Mineral*, 21:9–19 (1993).

Fujimoro, E., "Ultraviolet light–and ozone–induced changes in pyridinoline, a trisubstitued 3–Hydroxypyridinium crosslink of collagen," *Biochimica et Biophysica Acta* 828:104–106 (1985).

Sakura et al., "Photolysis of pyridinoline, a cross–linking amino acid of collagen, by ultraviolet light, " *Can. J. Biochem.* 60:525–529 (1982).

Sakura et al., "Electrochemical behavior of pyridinoline, a crosslinking amino acid of collagen," *J. Biochem.* 89:1541–1546 (1981).

Koob et al., Detection and Photolysis of Hydroxypyridinium Crosslinks in Cartilage Collagen *In Situ, Orthopaedic Transactions* 7(2):251–252 (1983).

Rosmalen et al., "Light sensitivity of deoxypyridinoline: implications for the collection of urine," J.B.M.R. 9(Suppl. 1):B421 (1994).

Baurain et al., "Photolysis of desmosine and isodesmosine by ultraviolet light," *Eur. J. Biochem* 67:155–164 (1976).

Blumsohn et al., "Effect of light and γ–irradiation on pyridinolines and telopeptides of type I collagen in urine," *Clinical Chemistry* 41(8):1195–1197 (1995).

Becker, U., Timpl, R., and Kuhn, K., "Carboxyterminal Antigenic Determinants of Collagen from Calf Skin: Localization within Discrete Regions of the Nonhelical Sequences," *Eur. J. Biochem.* 28:221–231 (1972).

Lane et al., "Immunofluorescent Localization of Structural Collagen Types in Endochondral Fracture Healing," *Orthopaedic Transactions*, VI(2):236 (1982).

Kuhn, K., "The Classical Collagens: Types I, II, and III," In: *Structure and Function of Collagen Types* (1987).

Rauterberg, J., "The C–Terminal Non–Helical Portion of the Collagen Molecule," *Clin. Ortho. Rel. Res.* 97:196–212 (1973).

Davril et al., "Photolysis of crosslinked peptides from elastin of porcine aorta", FEBS Letters, 98(1):128–134 (1979).

Otter et al., Type I Collagen α–1 Chain C–Telopeptide: Solution Structure Determined by 600–MHz Proton NMR Spectroscopy and Implications for Its Role in Collagen Fibrillogenesis, *Biochemistry*, 27:3560–3567 (1988).

van Hoek, et al., A Novel Polyclonal Antibody Against Deoxy–pyridinoline to be Used in a Radioimmunoassay, Second Workshop on Bisphosphonates, Davos, Switzerland, Apr. 14–16, 1994.

Fuller, F. and Boedtker, H., "Sequence Determination and Analysis of the 3' Region of Chicken Pro–α1(I) and Pro–α1_(I) Collagen Messenger Ribinucleic Acids Including the Carboxy–Terminal Propeptide Sequences," *Biochemistry* 20:996–1006 (1981).

Rosmalen et al., Light Sensitivity of Deoxypyridinoline: Implications for the Collection of Urine, Presented at the Sixteenth Annual Meeting of the American Society of Bone and Mineral Research, Sep. 9–13, 1994.

Gunja–Smith & Boucek, "Desmosines in human urine," *Biochem, J.* 193:915–918 (1981).

Tellerova et al., "Determination of larger urinary peptides in osteoarthrosis by high–performance liquid chromatography," *Scand J Rheumatology* 15:52–56 (1986).

Adam, M. and Z. Deyl, "Altered expression of collagen phenotype in osteoarthrosis," *Clinica Chimica Acta.*, 133:25–32 (1983).

Johnstone et al., Immunochemistry in Practice, Blackwell Scientific Publications, Oxford, U.K., 1987, pp. 48–65.

Robins and Duncan, "Cross–linking of collagen, " *Biochem. J.* 215:175–182.

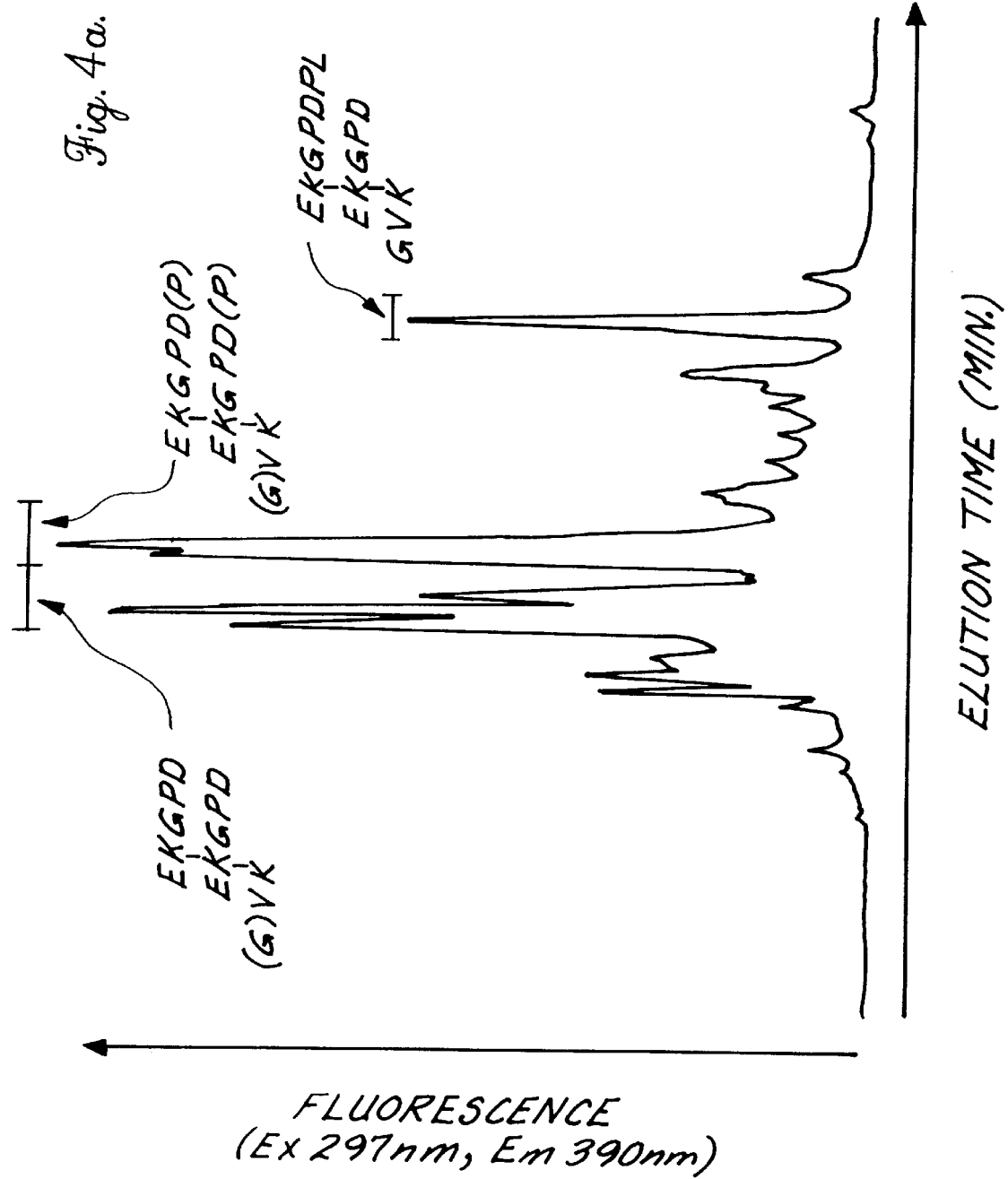

α1(I) Q L S Y G Y DE K S T G G I S V P G P M G P S G P R
α2(I) Q Y D G K G V G L G P G P M G L M G P R
         G I K G H R
          930

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide corresponding to the alpha2(I)
      N-telopeptide sequence of a cross-linked type I
      collagen metabolite, with the addition of a
      C-terminal cysteine

<400> SEQUENCE: 1

Gln Tyr Asp Gly Lys Gly Val Gly Cys
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide corresponding to the alpha2(I)
      N-telopeptide sequence of a cross-linked type I
      collagen metabolite, with the addition of a
      C-terminal cysteine

<400> SEQUENCE: 2

Tyr Asp Glu Lys Ser Thr Gly Gly Cys
 1               5

<210> SEQ ID NO 3
<211> LENGTH: 5
<212> TYPE: PRT
<213> ORGANISM: Homo sapiens

<400> SEQUENCE: 3

Gln Tyr Asp Gly Lys
 1               5

<210> SEQ ID NO 4
<211> LENGTH: 6
<212> TYPE: PRT
<213> ORGANISM: Homo sapiens

<400> SEQUENCE: 4

Gly Ile Lys Gly His Arg
 1               5
```

```
<210> SEQ ID NO 5
<211> LENGTH: 5
<212> TYPE: PRT
<213> ORGANISM: Homo sapiens

<400> SEQUENCE: 5

Glu Lys Gly Pro Asp
 1               5

<210> SEQ ID NO 6
<211> LENGTH: 6
<212> TYPE: PRT
<213> ORGANISM: Homo sapiens

<400> SEQUENCE: 6

Glu Lys Gly Pro Asp Pro
 1               5

<210> SEQ ID NO 7
<211> LENGTH: 7
<212> TYPE: PRT
<213> ORGANISM: Homo sapiens

<400> SEQUENCE: 7

Glu Lys Gly Pro Asp Pro Leu
 1               5
```

SYNTHETIC PEPTIDES CORRESPONDING TO TELOPEPTIDE SEQUENCES OF CROSS-LINKED TYPE II COLLAGEN METABOLITES

This is a continuation of prior application Ser. No. 09/237,176, filed Jan. 25, 1999, (U.S. Pat. No. 6,048,705) which is a continuation of Ser. No. 09/047,144, filed Mar. 24, 1998 (U.S. Pat. No. 5,962,639), which is a continuation of Ser. No. 08/803,960, filed Feb. 21, 1997 (abandoned), which is a continuation of Ser. No. 08/664,102, filed Jun. 13, 1996 (U.S. Pat. No. 5,677,198), which is a continuation of Ser. No. 08/567,618, filed Dec. 4, 1995 (U.S. Pat. No. 5,656,439), which is a continuation of Ser. No. 08/457,831, filed Jun. 1, 1995 (U.S. Pat. No. 5,576,189), which is a continuation of Ser. No. 08/221,705, filed Apr. 1, 1994 (U.S. Pat. No. 5.473,052), which is a continuation of Ser. No. 07/614,719, filed Nov. 21, 1990 (U.S. Pat. No. 5,300,434), which is a continuation-in-part of Ser. No. 07/444,881, filed Dec. 1, 1989 (U.S. Pat. No. 5,140,103), which is a continuation-in-part of Ser. No. 07/118,234, filed Nov. 6, 1987 (U.S. Pat. No. 4,973,666).

This invention was made with government support under grants AR37318 and AR36794 awarded by the National Institutes of Health. The government has certain rights in the invention.

FIELD OF THE INVENTION

The present invention relates to methods for detecting and monitoring collagen degradation in vivo. More specifically, it relates to methods for quantitating cross-linked telopeptides produced in vivo upon degradation of collagen types II and III.

BACKGROUND OF THE INVENTION

Three known classes of collagens have been described to date. The Class I collagens, subdivided into types I, II, III, V, and XI, are known to form fibrils. These collagens are all synthesized as procollagen molecules, made up of N-terminal and C-terminal propeptides, which are attached to the core collagen molecule. After removal of the propeptides, which occurs naturally in vivo during collagen synthesis, the remaining core of the collagen molecule consist largely of a triple-helical domain having terminal telopeptide sequences which are nontriple-helical. These telopeptide sequences have an important function as sites of intermolecular cross-linking of collagen fibrils extracellularly.

The present invention relates to methods of detecting collagen degradation based on assaying for particular cross-linked telopeptides produced in vivo upon collagen degradation. In the past, assays have been developed for monitoring degradation of collagen in vivo by measuring various biochemical markers, some of which have been degradation products of collagen. For example, bone turnover associated with Paget's disease has been monitored by measuring small peptides containing hydroxyproline, which are excreted in the urine following degradation of bone collagen. Russell et al., *Metab. Bone Dis. and Rel. Res.* 4 and 5, 255–262 (1981); and Singer, F. R., et al., *Metabolic Bone Disease*, Vol. II (eds. Avioli, L. V. and Kane, S. M.), 489–575 (1978), Academic Press, New York.

Other researchers have measured the cross-linking compound pyridinoline in urine as an index of collagen degradation in joint disease. See, for background and for example, Wu and Eyre, *Biochemistry*, 23:1850 (1984); Black et al., *Annals of the Rheumatic Diseases*, 48:641–644 (1989); Robins et al.; *Annals of the Rheumatic Diseases*, 45:969–973 (1986); and Seibel et al., *The Journal of Rheumatology*, 16:964 (1989). In contrast to the present invention, some prior researchers have hydrolyzed peptides from body fluids and then looked for the presence of individual hydroxypyridinium residues. None of these researchers has reported measuring a telopeptide containing a cross-link that is naturally produced in vivo upon collagen degradation, as in the present invention.

U.K. Patent application GB 2,205,643 reports that the degradation of type III collagen in the body is quantitatively determined by measuring the concentration of an N-terminal telopeptide from type III collagen in a body fluid. In this reference, it is reported that cross-linked telopeptide regions are not desirable. In fact, this reference reports that it is necessary to use a non-cross-linked source of collagen to obtain the telopeptide. The peptides of the present invention are all cross-linked. Collagen cross-links are discussed in greater detail below, under the heading "Collagen Cross-Linking."

There are a number of reports indicating that collagen degradation can be measured by quantitating certain procollagen peptides. The present invention involves telopeptides rather than propeptides, the two being distinguished by their location in the collagen molecule and the timing of their cleavage in vivo. See U.S. Pat. No. 4,504,587; U.S. Pat. No. 4,312,853; Pierard et al., *Analytical Biochemistry* 141:127–136 (1984); Niemela, *Clin. Chem.*, 31/8:1301–1304 (1985); and Rohde et al., *European Journal of Clinical Investigation*, 9:451–459 (1970).

U.S. Pat. No. 4,778,768 relates to a method of determining changes occurring in articular cartilage involving quantifying proteoglycan monomer or antigenic fragments thereof in a synovial fluid sample. This patent does not relate to detecting cross-linked telopeptides derived from degraded collagen.

Dodge, *J. Clin. Invest.*, 83:647–661 (1981) discloses methods for analyzing type II collagen degradation utilizing a polygonal antiserum that specifically reacts with unwound alpha-chains and cyanagen bromide-derived peptides of human and bovine type II collagens. The peptides involved are not cross-linked.

Amino acid sequences of human type III collagen, human proα1(II) collagen, and the entire preproα1(III) chain of human type III collagen and corresponding cDNA clones have been investigated and determined by several groups of researchers. See Loidi et al., *Nucleic Acids Research* 12:9383–9394 (1984); Sangiorgi et al., *Nucleic Acids Research*, 13:2207–2225 (1985); Baldwin et al., *Biochem. J.*, 262:521–528 (1989); and Ala-Kokko et al., *Biochem. J.*, 260:509–516 (1989). None of these references specifies the structures of particular telopeptide degradation products that could be measured to determine the amount of degraded fibrillar collagen in vivo.

In spite of the above-described background information, there remains a need for effective and simple assays for determining collagen degradation in vivo. Such assays could be used to detect and monitor disease states in humans, such as osteoarthritis (type II collagen degradation), and various inflammatory disorders, such as vasculitis syndrome (type III collagen degradation).

Assays for type I collagen degradation, described in the parent application, U.S. Ser. No. 118,234, can be utilized to detect and assess bone resorption in vivo. Detection of bone resorption may be a factor of interest in monitoring and detecting diseases such as osteoporosis. Osteoporosis is the most common bone disease in man. Primary osteoporosis, with increased susceptibility to fractures, results from a progressive net loss of skeletal bone mass. It is estimated to affect 15–20 million individuals in the United States. Its basis is an age-dependent imbalance in bone remodeling, i.e., in the rates of synthesis and degradation of bone tissue.

About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., Science, 236:914 (1987)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, no method is available for measuring bone resorption rates in patients or normal subjects. A major difficulty in monitoring the disease is the lack of a specific assay for measuring bone resorption rates.

Methods for assessing bone mass often rely on measuring whole-body calcium by neutron activation analysis or mineral mass in a given bone by photon absorption techniques. These measurements can give only long-term impressions of whether bone mass is decreasing. Measuring calcium balances by comparing intake with output is tedious, unreliable and can only indirectly appraise whether bone mineral is being lost over the long term. Other methods currently available for assessing decreased bone mass and altered bone metabolism include quantitative scanning radiometry at selected bone locations (wrist, calcaneus, etc.) and histomorphometry of iliac crest biopsies. The former provides a crude measure of the bone mineral content at a specific site in a single bone. Histomorphometry gives a semi-quantitative assessment of the balance between newly deposited bone seams and resorbing surfaces.

A urinary assay for the whole-body output of degraded bone in 24 hours would be much more useful. Mineral studies (e.g., calcium balance) cannot do this reliably or easily. Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as pointed out above. For this reason, urinary hydroxyproline has been used extensively as an amino acid marker for collagen degradation. Singer, F. R., et al. (1978), cited hereinabove.

U.S. Patent No. 3,600,132 discloses a process for determination of hydroxyproline in body fluids such as serum, urine, lumbar fluid and other intercellular fluids in order to monitor deviations in collagen metabolism. In particular, this inventor notes that in pathologic conditions such as Paget's disease, Marfan's syndrome, osteogenesis imperfecta, neoplastic growth in collagen tissues and in various forms of dwarfism, increased collagen anabolism or catabolism as measured by hydroxyproline content in biological fluids can be determined. This inventor measures hydroxyproline by oxidizing it to a pyrrole compound with hydrogen peroxide and N-chloro-p-toluenesulphonamide followed by calorimetric determination in p-dimethyl-amino-benzaldehyde.

In the case of Paget's disease, the increased urinary hydroxyproline probably comes largely from bone degradation; hydroxyproline, however, generally cannot be used as a specific index. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline. Furthermore, about 80% of the free hydroxyproline derived from protein degradation is metabolized in the liver and never appears in the urine. Kiviriko, K. I. Int. Rev. Connect. Tissue Res. 5:93 (1970), and Weiss, P. H. and Klein, L., J. Clin. Invest. 48: 1 (1969).

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption. Krane, S. M. and Simon, L. S. Develop. Biochem., 22:185 (1981).

In addition to amino acids unique to collagen, various non-collagenous proteins of bone matrix such as osteocalcin, or their breakdown products, have formed the basis of immunoassays aimed at measuring bone metabolism. Price, P. A. et al. J. Clin. Invest., 66: 878 (1980), and Gundberg, C. M. et al., Meth. Enzymol., 107:516 (1984). However, it is now clear that bone-derived non-collagenous proteins, though potentially a useful index of bone metabolic activity are unlikely, on their own, to provide quantitative measures of bone resorption. The concentration in serum of osteocalcin, for example, fluctuates quite widely both normally and in metabolic bone disease. Its concentration is elevated in states of high skeletal turnover but it is unclear whether this results from increased synthesis or degradation of bone. Krane, S. M., et al., Develop. Biochem., 22:185 (1981), Price, P. A. et al., J. Clin. Invest., 66:878 (1980); and Gundberg, C. M. et al., Meth. Enzymol., 107:516 (1984).

Collagen Cross-Linking

The polymers of most genetic types of vertebrate collagen require the formation of aldehyde-mediated cross-links for normal function. Collagen alde-hydes are derived from a few specific lysine or hydroxylysine side-chains by the action of lysyl oxidase. Various di-, tri- and tetrafunctional cross-linking amino acids are formed by the spontaneous intra- and intermolecular reactions of these aldehydes within the newly formed collagen polymers; the type of cross-linking residue varies specifically with tissue type (see Eyre, D. R. et al., Ann. Rev. Biochem., 53:717–748 (1984)).

Two basic pathways of cross-linking can be differentiated for the banded (67 nm repeat) fibrillar coliagens, one based on lysine aldehydes, the other on hydroxylysine aldehydes. The lysine aldehyde pathway dominates in adult skin, cornea, sciera, and rat tail tendon and also frequently occurs in other soft connective tissues. The hydroxylysine aldehyde pathway dominates in bone, cartilage, ligament, most tendons and most internal connective tissues of the body, Eyre, D. R. et at. (1974) vida supra. The operating pathway is governed by whether lysine residues are hydroxylated in the telopeptide sites where aldehyde residues will later be formed by lysyl oxidase (Barnes, M. J. et al., Biochem J., 139:461 (1974)).

The chemical structure(s) of the mature cross-linking amino acids on the lysine aldehyde pathway are unknown, but hydroxypyridinium residues have been identified as mature products on the hydroxylysine aldehyde route. On both pathways and in most tissues the intermediate, borohydride-reducible cross-linking residues disappear as the newly formed collagen matures, suggesting that they are relatively short-lived intermediates (Bailey, A. J. et al., *FEBS Lett.*, 16:86 (1971)). Exceptions are bone and dentin, where the reducible residues persist in appreciable concentration throughout life, in part apparently because the rapid mineralization of the newly made collagen fibrils inhibits further spontaneous cross-linking interactions (Eyre, D. R., *In: The Chemistry and Biology of Mineralized Connective Tissues*, (Veis, A. ed.) pp. 51–55 (1981), Elsevier, New York, and Walters, C. et al., *Calc. Tiss. Intl.*, 35:401–405 (1983)).

Two chemical forms of 3-hydroxypyridinium cross-link have been identified (Formula I and II). Both compounds are naturally fluorescent, with the same characteristic excitation and emission spectra (Fujimoto, D. et al. *Biochem. Biophys. Res. Commun.*, 76:1124 (1977), and Eyre, D. R., *Develop. Biochem.*, 22:50 (1981)). These amino acids can be resolved and assayed directly in tissue hydrolysates with good sensitivity using reverse phase HPLC and fluorescence detection. Eyre, D. R. et al., *Analyte. Biochem.*, 137:380–388 (1984). It should be noted that the present invention involves quantitating particular peptides rather than amino acids.

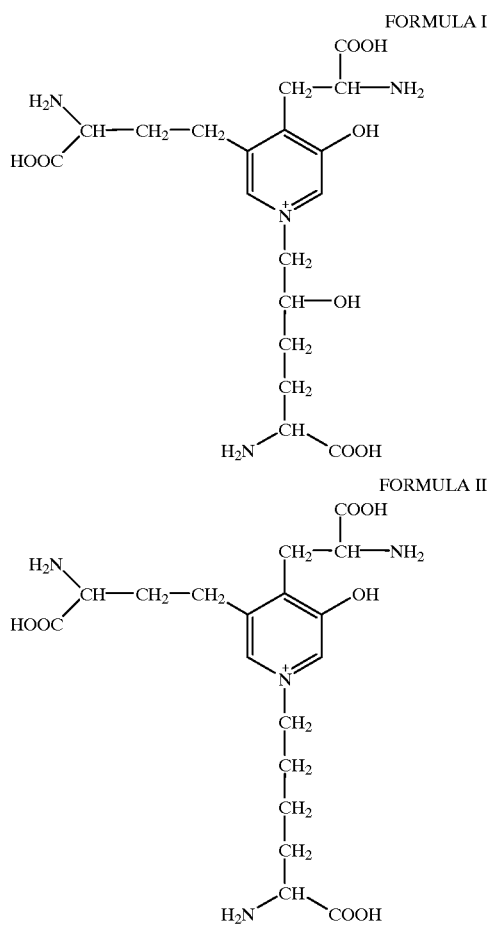

In growing animals, it has been reported that these mature cross-links may be concentrated more in an unmineralized fraction of bone collagen than in the mineralized collagen (Banes, A. J., et al., *Biochem. Biophys. Res. Commun.*, 113:1975 (1983). However, other studies on young bovine or adult human bone do not support this concept, Eyre, D. R., *In: The Chemistry and Biology of Mineralized Tissues* (Butler, W. T. ed.) p.105 (1985), Ebsco Media Inc., Birmingham, Ala.

The presence of collagen hydroxypyridinium cross-links in human urine was first reported by Gunja-Smith and Boucek (Gunja-Smith, Z. and Boucek, R. J., *Biochem J.*, 197:759–762 (1981)) using lengthy isolation procedures for peptides and conventional amino acid analysis. At that time, they were aware only of the HP form of the cross-link. Robins (Robins, S. P., *Biochem J.*, 207:617–620 (1982) has reported an enzyme-linked immunoassay to measure HP in urine, having raised polyclonal antibodies to the free amino acid conjugated to bovine serum albumin. This assay is intended to provide an index for monitoring increased joint destruction that occurs with arthritic diseases and is based, according to Robins, on the finding that pyridinoline is much more prevalent in cartilage than in bone collagen.

In more recent work involving enzyme-linked immunoassay, Robins reports that lysyl pyridinoline is unreactive toward antiserum to pyridinoline covalently linked to bovine serum albumin (Robins et al., *Ann. Rheum. Diseases*, 45:969–973 (1986)). Robins' urinary index for cartilage destruction is based on the discovery that hydroxylysyl pyridinoline, derived primarily from cartilage, is found in urine at concentrations proportional to the rate of joint cartilage resorption (i.e., degradation). In principle, this index could be used to measure whole body cartilage loss; however, no information on bone resorption would be available.

A need therefore exists for a method that allows the measurement of whole-body bone resorption rates in humans. The most useful such method would be one that could be applied to body fluids, especially urine. The method should be sensitive, i.e., quantifiable down to 1 picomole and rapidly measure 24-hour bone resorption rates so that the progress of various therapies (e.g., estrogen) can be assessed.

SUMMARY OF THE INVENTION

The present invention is based on the discovery of the presence of particular cross-linked telopeptides in body fluids of patients and normal human subjects. These telopeptides are produced in vivo during collagen degradation and remodeling. The term "telopeptides" is used in a broad sense herein to mean cross-linked peptides having sequences that are associated with the telopeptide region of, e.g., type II and type III collagens and which may have cross-linked to them a residue or peptide associated with the collagen triple-helical domain. Generally, the telopeptides disclosed herein will have fewer amino acid residues than the entire telopeptide domains of type II and type II collagens. Typically, the telopeptides of the present invention will comprise two peptides linked by a pyridinium cross-link and further linked by a pyridinium cross-link to a residue or peptide of the collagen triple-helical domain. Having disclosed the structures of these telopeptides herein, it will be appreciated by one of ordinary skill in the art that they may also be produced other than in vivo, e.g., synthetically. These peptides will generally be provided in purified form, e.g., substantially free of impurities, particularly other peptides.

The present invention also relates to methods for determining in vivo degradation of type II and type III collagens. The methods involve quantitating in a fluid the concentration of particular telopeptides that have a 3-tiydroxypyridinium cross-link and that are derived from collagen degradation. The methods disclosed in the present invention are analogous to those previously disclosed in U.S. Ser. No. 118,234, filed Nov. 6, 1987, for determining the absolute rate of bone resorption in vivo. Those methods involved quantitating in a body fluid the concentration of telopeptides having a 3-hydroxypyridinium cross-link derived from bone collagen resorption.

In a representative assay, the patient's body fluid is contacted with an immunological binding partner specific to a telopeptide having a 3-hydroxypyridinium cross-link derived from type II or type III collagen. The body fluid may be used as is or purified prior to the contacting step. This purification step may be accomplished using a number of standard procedures, including cartridge adsorption and elution, molecular sieve chromatography, dialysis, ion exchange, alumina chromatography, hydroxyapatite chromatography, and combinations thereof.

Other representative embodiments of quantitating the concentration of peptide fragments having a 3-hydroxypyridinium cross-link in a body fluid include electrochemical titration, natural fluorescence spectroscopy, and ultraviolet absorbance. Electrochemical titration may be conducted directly upon a body fluid without further purification. However, when this is not possible due to excessive quantities of contaminating substances, the body fluid is first purified prior to the electrochemical titration step. Suitable methods for purification prior to electrochemical detection include dialysis, ion exchange chromatography, alumina chromatography, molecular sieve chromatography, hydroxyapatite chromatography and ion exchange absorption and elution.

Fluorometric measurement of a body fluid containing a 3-hydroxypyridinium cross-link is an alternative way of quantitating collagen degradation (and, hence, bone resorption, if type I peptides are quantitated). The fluorometric assay can be conducted directly on a body fluid without further purification. However, for certain body fluids, particularly urine, it is preferred that purification of the body fluid be conducted prior to the fluorometric assay. This purification step consists of dialyzing an aliquot of a body fluid such as urine against an aqueous solution thereby producing partially purified peptide fragments retained within the nondiffusate (retentate). The nondiffusate is then lyophilized, dissolved in an ion pairing solution and adsorbed onto an affinity chromatography column. The chromatography column is washed with a volume of ion pairing solution and, thereafter, the peptide fragments are eluted from the column with an eluting solution. These purified peptide fragments may then be hydrolyzed and the hydrolysate resolved chromatographically. Chromatographic resolution may be conducted by either high-performance liquid chromatography or microbore high performance liquid chromatography.

The invention includes peptides having structures identical to peptides derived from collagen degradation, substantially free from other human peptides, which may be obtained from a body fluid. The peptides contain at least one 3-hydroxypyridinium cross-link, in particular, a lysyl pyridinoline cross-link or a hydroxylysyl pyridinoline cross-link, arid are derived from the telopeptide region of type II or type III collagen linked to one or more residues from a triple-helical domain, typically by the action of endogenous proteases and/or peptidases.

The structures of the type II and type III telopeptides are, disclosed below. Information on tile type I telopeptides, originally presented in U.S. Ser. No. 118,234, is also included.

Another aspect of the present invention involves assays for the peptides described herein in which the pyridinium rings are intact and cleaved. Since it is suspected that some cleavage of pyridinium rings occurs in vivo, assays that detect both intact and cleaved pyridinium rings may lead to more accurate assessments of collagen degradation. In connection with this aspect of tile present invention, specific binding partners to the individual peptides containing intact or cleaved pyridinium rings, may be employed in the assays. Individual specific binding partners that recognize both types of peptides (both intact and cleaved pyridinium ring containing peptides) may be employed. Alternatively, specific binding partners that discriminate between peptides containing the intact pyridinium ring and those in which the pyridinium ring is cleaved, could also be used.

Structure of Cross-Linked Telopeptides Derived from Type I Collagen

A specific telopeptide having a 3-hydroxypyridinium cross-link derived from the N-terminal (amino-terminal) telopeptide domain of bone type I collagen has the following amino acid sequence:

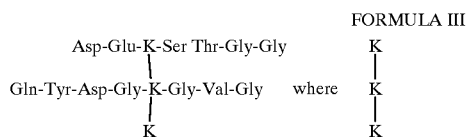

FORMULA III is hydroxylysyl pyridinoline or lysyl pyridinoline, and Gln is glutamine or pyrrolidine carboxylic acid.

The invention also encompasses a peptide containing at least one 3-hydroxypyridinium cross-link derived from the C-terminal (carboxy-terminal) telopeptide domain of bone type I collagen. These C-terminal telopeptide sequences are cross-linked with either lysyl pyridinoline or hydroxylysyl pyridinoline. An example of such a peptide sequence is represented by the formula:

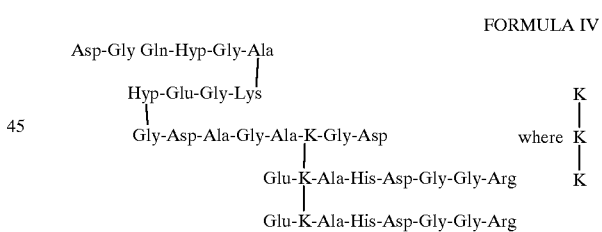

FORMULA IV is hydroxylysyl or lysyl pyridinoline.

Since the filing of U.S. Ser. No. 118,234, the inventor has discovered evidence of two additional type I collagen telopeptides in body fluids, having the following structures:

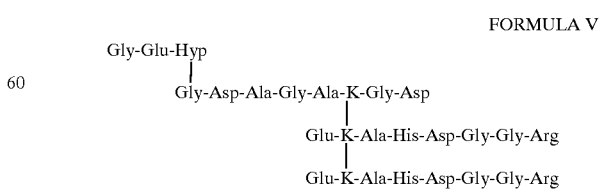

FORMULA V and

FORMULA VI

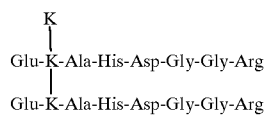

These telopeptides may also be quantitated in body fluids in accordance with the present invention.

Structure of a Cross-Linked Telopeptide Derived from Type II Collagen

A specific telopeptide having a hydroxylysyl pyridinoline cross-link derived from the C-terminal telopeptide domain of type II collagen has the following amino acid sequence (referred to hereinbelow as the core peptide structure):

FORMULA VII

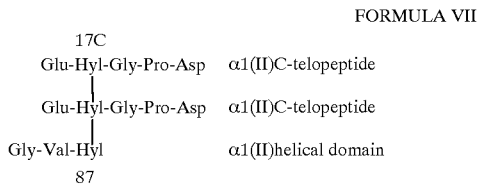

wherein the cross-linking residue depicted as Hyl-Hyl-Hyl is hydroxylysyl pyridinoline (HP), a natural 3-hydroxypyridinium residue present in mature collagen fibrils of various tissues.

Amino-terminal telopeptides from type II collagen have not been detected in body fluids, and it is suspected that potential peptides derived from the N-terminal telopeptide region of type II collagen are substantially degraded in vivo, perhaps all the way to the free HP cross-linking amino acid.

Structure of Cross-Linked Telopeptides Derived from Type III Collagen

By analogy to the above disclosure, cross-linked peptides that are derived from proteolysis of human type III collagen may be present in body fluids. These peptides have a core structure embodied in the following parent structures:

FORMULA VIII

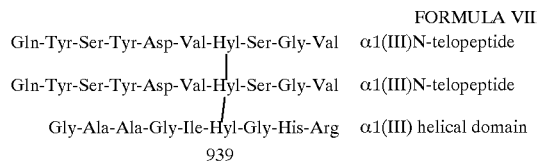

and

FORMULA IX

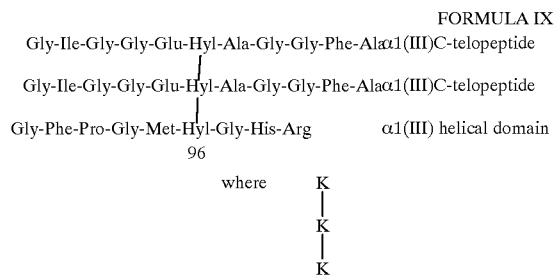

is hydroxylysyl or lysyl pyridinoline, and Gln is glutamine or pyrrolidine carboxylic acid.

A likely cross-linked peptide derived from type III collagen in body fluids has the core structure:

FORMULA X

that is derived from two α1(III)N-telopeptide domains linked to an hydroxylysyl pyridinoline residue (Hyl-Hyl-Hyl).

A second possible fragment of the C-telopeptide cross-linking domain, based on the collagen types I and II peptides observed in urine, has the core structure:

FORMULA XI

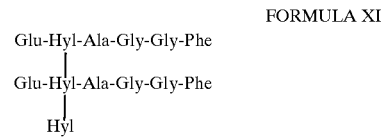

Smaller and larger versions (differing by one to three amino acids on each component chain) of these two peptides corresponding to the parent sequences shown above (FORMULAE VIII and IX) may also be present and measurable in body fluids. Analogous smaller and larger versions of each of the peptides disclosed herein form part of the present invention as well.

The invention generally includes all specific binding partners to the peptides described herein. "Specific binding partners" are molecules that are capable of binding to the peptides of the present invention. Included within this term are immunological binding partners, such as antibodies (monoclonal and polyclonal), antigen-binding fragments of antibodies (e.g., Fab and F(ab')$_2$ fragments), single-chain antigen-binding molecules, and the like, whether made by hybridoma or rDNA technologies.

The invention includes fused cell hybrids (hybridomas) that produce monoclonal antibodies specific for the above-described collagen peptides having 3-hydroxypyridinium cross-links (both with an intact pyridinium ring and one that has been cleaved).

The invention further includes monoclonal antibodies produced by the fused cell hybrids, and those antibodies (as well as binding fragments thereof, e.g., Fab) coupled to a detectable marker. Examples of detectable markers include enzymes, chromophores, fluorophores, coenzymes, enzyme inhibitors, chemiluminescent materials, paramagnetic metals, spin labels, and radioisotopes. Such specific binding partners may alternatively be coupled to one member of a ligand-binding partner complex (e.g., avidin-biotin), in which case the detectable marker can be supplied bound to the complementary member of the complex.

The invention also includes test kits useful for quantitating the amount of peptides having 3-hydroxypyridinium cross-links derived from collagen degradation in a body fluid. The kits may include a specific binding partner to a peptide derived from degraded collagen as disclosed herein. The specific binding partners of the test kits may be coupled to a detectable marker or a member of a ligand binding partner complex, as described above.

BRIEF DESCRIPTION OF THE DRAWINGS

FIG. 4A shows relative fluorescence (297 nm excitation, 390 nm emission) versus elution time of fractions during reverse phase HPLC. Cross-linked type II collagen telopeptides are eluted as indicated. The fractions indicated by the bar (-) show evidence by sequence and composition analysis of the peptides indicated that retain or have lost the gly (G) and pro (P) residues.

DETAILED DESCRIPTION OF THE PREFERRED EMBODIMENT

Type II Collagen Telopeptides

Figure 1:
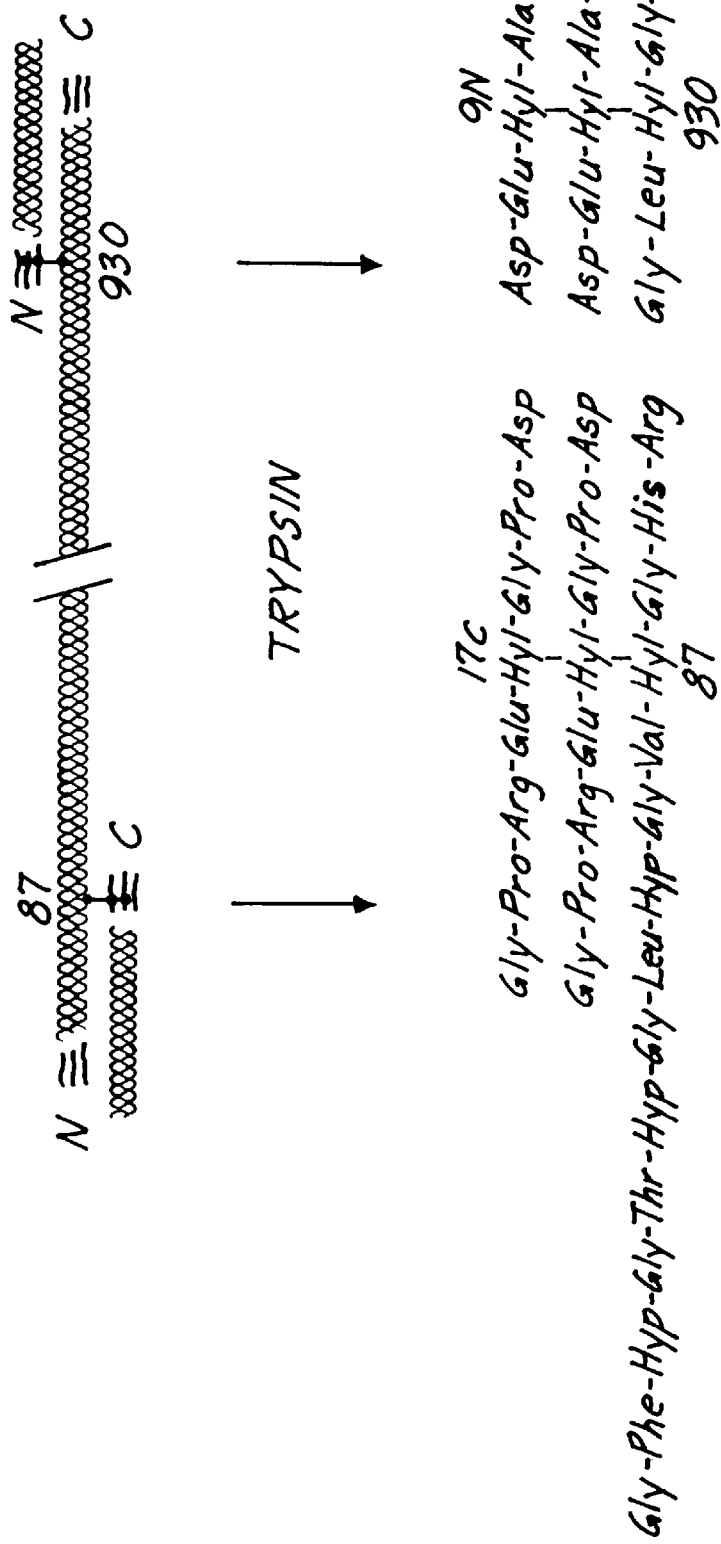
FIG. 1 is a depiction of type II collagen and a proposal for the source of telopeptides. It is not established whether the two telopeptides shown come from one collagen molecule as depicted in FIG. 1 or from two collagen molecules.

The core peptide structure of the type II cohlagen peptides may be found in body fluids as a component of larger peptides that bear additional amino acids or amino acid sequences on one or more ends of the three peptide sequences joined by the HP residue. FIG. 1 shows how type II collagen telopeptides, which are linked to a triple-helical sequence, may be produced in vivo from a human source using the proteolytic enzymes pepsin and trypsin. Smaller fragments that have lost amino acids from the core peptide structure, particularly from the helical sequence, may also occur in body fluids. Generally, additions or deletions of amino acids from the core peptide structure will involve from 1 to about 3 amino acids. Additional amino acids will generally be determined by the type It collagen telopeptide sequence that occurs naturally in vivo. As examples, peptides having the following structure:

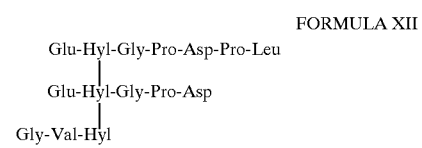

FORMULA XII and

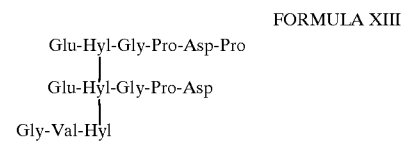

FORMULA XIII can be isolated chromatographically from urine, and another of structure:

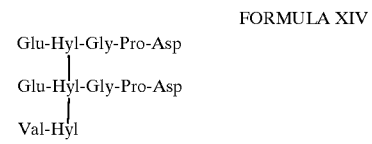

FORMULA XIV may also be isolated. In addition, glycosylated variants of the core structure and its larger and smaller variants may occur in which a galactose residue or a glucosyl galactose residue are attached to the side chain hydroxyl group of the HP cross-linking residue. Each peak in the graph shown in FIGS. 4A and 4B may correspond to a cross-linked fragment of particular structure that may be quantitated for purposes of the present invention.

These structures are consistent with their site of origin in human type II collagen fibrils at a molecular cross-linking site formed between two α1(II) C-telopeptides and residue 87 of a triple-helical domain, the known sequences about which are:

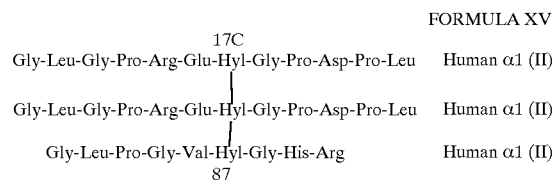

FORMULA XV

The isolated peptide fragments represent the products of proteolytic degradation of type II collagen fibrils within the body. The core structure containing the HP residue is relatively resistant to further proteolysis and provides a quantitative measure of the amount of type II collagen degraded.

Collagen type II is present in hyaline cartilage of joints in the adult skeleton. Quantitation of the collagen type II telopeptides in a body fluid, for example by way of a monoclonal antibody that recognizes an epitope in the peptide structure, would provide a quantitative measure of whole-body cartilage destruction or remodeling. In a preferred embodiment, the present invention involves an assay for cartilage tissue degradation in humans based on quantifying the urinary excretion rate of at least one member of this family of telopeptides. Such an assay could be used, for example, to:

(1) screen adult human subjects for those individuals having abnormally high rates of cartilage destruction as an early diagnostic indicator of osteoarthritis;

(2) monitor the effects of potential antiarthritic drugs on cartilage metabolism in osteoarthritic and rheumatoid arthritic patients; or (3) monitor the progress of degenerative joint disease in patients with osteoarthritis and rheumatoid arthritis and their responses to various therapeutic interventions.

Osteoarthritis is a degenerative disease of the articulating cartilages of joints. In its early stages it is largely non-inflammatory (i.e. distinct from rheumatoid arthritis). It is not a single disease but represents the later stages of joint failure that may result from various factors (e.g. genetic predisposition, mechanical over usage, joint malformation or a prior injury, etc.). Destruction of joint articular cartilage is the central progressive feature of osteoarthritis. The incidence of osteoarthritis, based on radiographic surveys, ranges from 4% in the 18–24 year age group to 85% in the 75–79 year age group. At present the disease can only be diagnosed by pain and radiographic or other imaging signs of advanced cartilage erosion.

The assays disclosed above may be used to detect early evidence of accelerated cartilage degradation in mildly symptomatic patients, to monitor disease progress in more advanced patients, and as a means of monitoring the effects of drugs or other therapies.

In normal young adults (with mature skeletons) there is probably very little degradation of cartilage collagen. A test that could measure fragments of cartilage collagen in the urine (and in the blood and joint fluid) would be very useful for judging the "health" of cartilage in the whole body and in individual joints. The type II collagen-specific peptide assays described above will accomplish this. In the long term, such an assay could become a routine diagnostic screen for spotting those individuals whose joints are wearing away. They could be targeted early on for preventative therapy, for example, by the next generation of so-called chondroprotective drugs now being evaluated by the major pharmaceutical companies who are all actively seeking better agents to treat osteoarthritis.

Other diseases in which joint cartilage is destroyed include: rheumatoid arthritis, juvenile rheumatoid arthritis, ankylosing spondylitis, psoriatic arthritis, Reiter's syndrome, relapsing polychondritis, the low back pain syndrome, and other infectious forms of arthritis. The type II collagen-specific assays described herein could be used to diagnose and monitor these diseases and evaluate their response to therapy, as disclosed above in connection with osteoarthritis.

Type III Collagen Telopeptides

As pointed out above, human type III collagen telopeptides that may be present in body fluids are expected to have a core structure embodied in the following parent structures:

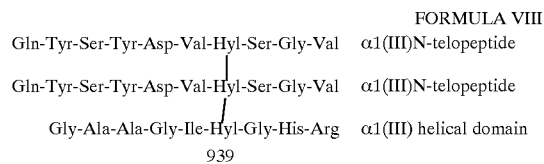

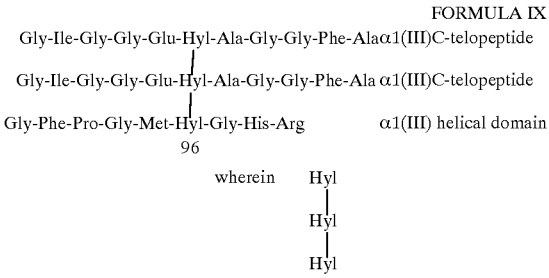

is hydroxylysyl pyridinoline.

By analogy to the type II peptides, the type III collagen peptides may occur in glycosylated forms of the core structure. For example, galactose residues or glucosylgalactose residues may be attached to the core structure, e.g. by way of hydroxyl groups.

The cross-linking residue of the type III collagen peptides is depicted as a 3-hydroxypyridinium residue, hydroxylysyl pyridinoline. The type II telopeptide structures have been found to primarily have hydroxylysyl pyridinoline cross-linking residues. However, whereas the type II collagen peptides are derived from the N-terminal telopeptide region of type II collagen, the type III collagen peptides may be derived from either the N-terminal or the C-terminal of type III collagen, as long as at least one cross-linking residue is present.

Type III collagen is present in many connective tissues in association with type I collagen. It is especially concentrated in vascular walls, in the skin and in, for example, the synovial membranes of joints where its accelerated turnover might be observed in inflammatory joint diseases such as rheumatoid arthritis.

A specific assay for type III collagen degradation by quantitating cross-linked type III collagen peptides as disclosed above, can be used for detecting, diagnosing, and monitoring various inflammatory disorders, possibly with particular application to the vasculitis syndromes. In conjunction with assays for measuring bone type I and cartilage type II collagen degradation rates, such an assay could be used as a differential diagnostic tool for patients with various degenerative and inflammatory disorders that result in connective tissue destruction or pathological processes.

Isolation of Type II and Type III Collagen Telopeptides

General Procedure:

Urine is collected form a normal adolescent during a rapid phase of skeletal growth. Using a sequence of chromatographic steps that include but are not limited to, adsorption on selective cartridges of a hydrophobic interaction support and an ion-exchange support and molecular sieve, ion-exchange and reverse-phase HPLC column chromatography steps, individual peptides are isolated. The cross-linked peptides containing HP (and LP) residues are detected during column chromatography by their natural fluorescence (Ex max 297 nm <pH 4, Ex max 330 nm, >pH 6; Em max 390 nm). An exemplary isolation procedure is provided in the Example below.

Specific Example:

Fresh urine (at 4° C.) diluted 5 times with water and adjusted to 2% (v/v) trifluoroacetic acid, passed through a C-18 hydrophobic binding cartridge (Waters C-18 Sep-pak prewetted with 80% (v/v) acetonitrile then washed with water). Retained peptides were washed with water then eluted with 3 ml of 20% (v/v) acetonitrile, and this eluent was adjusted to 0.05 M $NH_4HCO_3$, 10% (v/v) acetonitrile by addition of an equal volume of 0.1 M $NH_4HCO_3$. This solution was passed through a QMA-Sep-pak (Waters), which was washed with 10 ml of 0.1M NaCl, 20% (v/v) acetonitrile followed by 10 ml of water and the peptides were then eluted with 3 ml of 1% (v/v) trifluoroacetic acid and dried by Speed-Vac (Savant).

Figure 2:
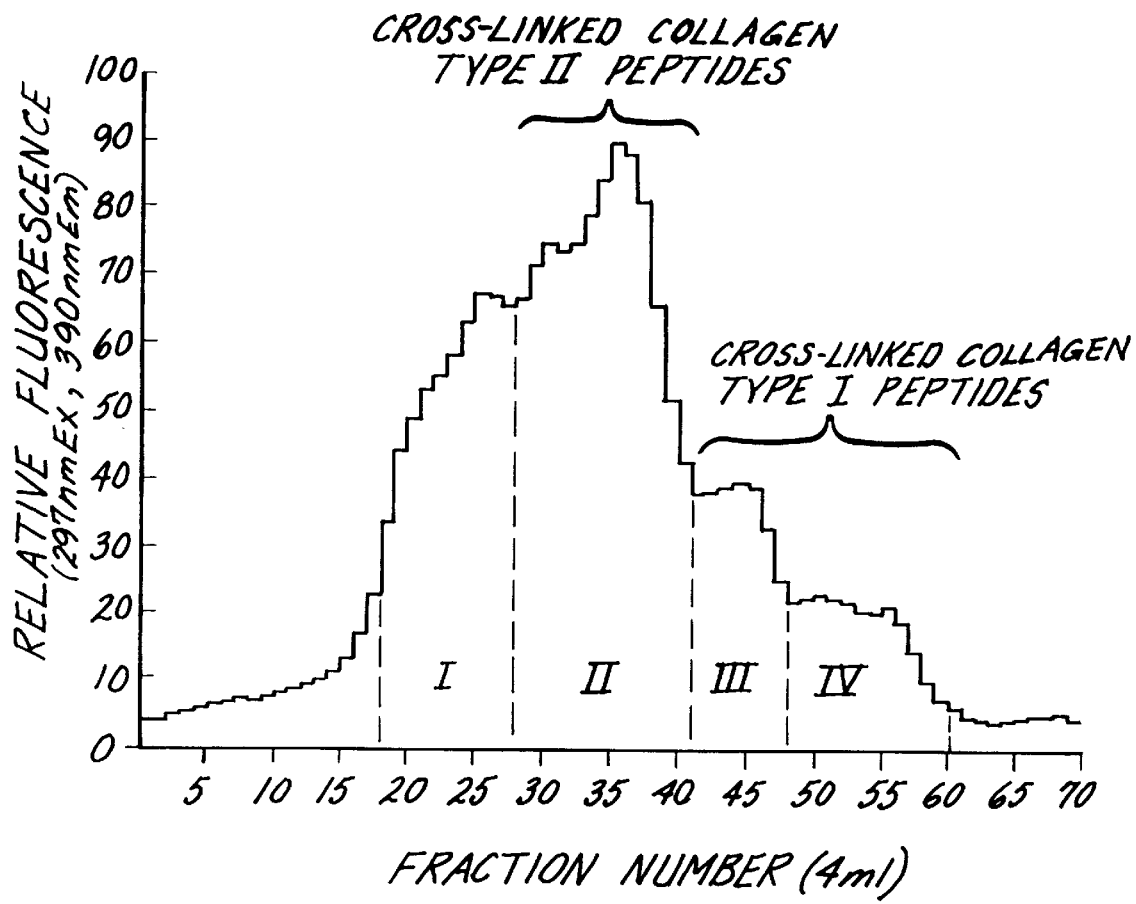
FIG. 2 shows relative fluorescence (297 nm excitation; 390 nm emission) versus fraction number (4 ml), obtained during molecular sieve chromatographic purification of cross-linked telopeptides. Cross-linked type II collagen telopeptides are contained in the fractions designated II.

Peptides were fractionated in three chromatographic steps. The first step was molecular sieve chromatography on a column of Bio-Gel P-10 (Bio Rad Labs, 2.5 cm×90 cm) eluted by 10% (v/v) acetic acid, monitoring the effluent for HP fluorescence as shown in FIG. 2. In FIG. 2, the Y-axis is the relative fluorescence emission at 390 nm (297 nm excitation), and the X-axis is the fraction number. The fraction size was 4 ml. The fractions indicated as II are enriched in the cross-linked collagen type II telopeptides. The cross-linked collagen type I telopeptides are contained in the fractions indicated as III and IV. Fractions spanning pool II (enriched in the type II collagen cross-linked peptides) were combined, freeze-dried and fractionated by ion-exchange column chromatography on a DEAE-HPLC column (TSK-DEAE-5PW, 7.5 mm×7.5 mm, Bio-Rad Labs), equilibrated with 0.02 M Tris/HCl, 10% (v/v) acetonitrile, pH 7.5 and eluted with a gradient of 0–0.5M NaCl in the same buffer as shown in FIG. 2.

Figure 3A:
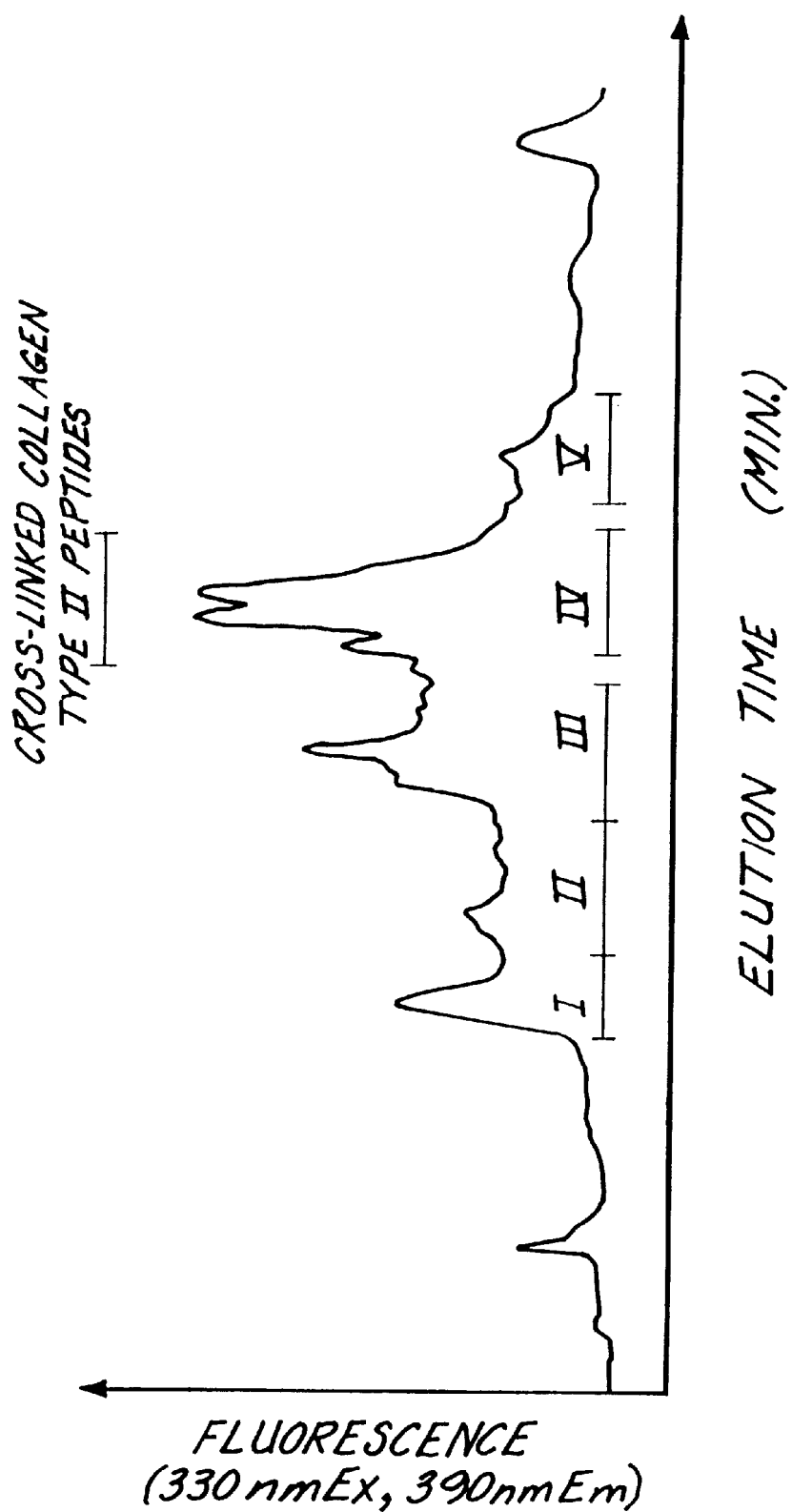
FIG. 3A shows relative fluorescence (330 nm excitation, 390 nm emission) versus elution time of fractions during ion exchange HPLC (DEAE-5PW). Cross-linked type II collagen telopeptides are contained in the fraction designated IV.
Figure 3B:
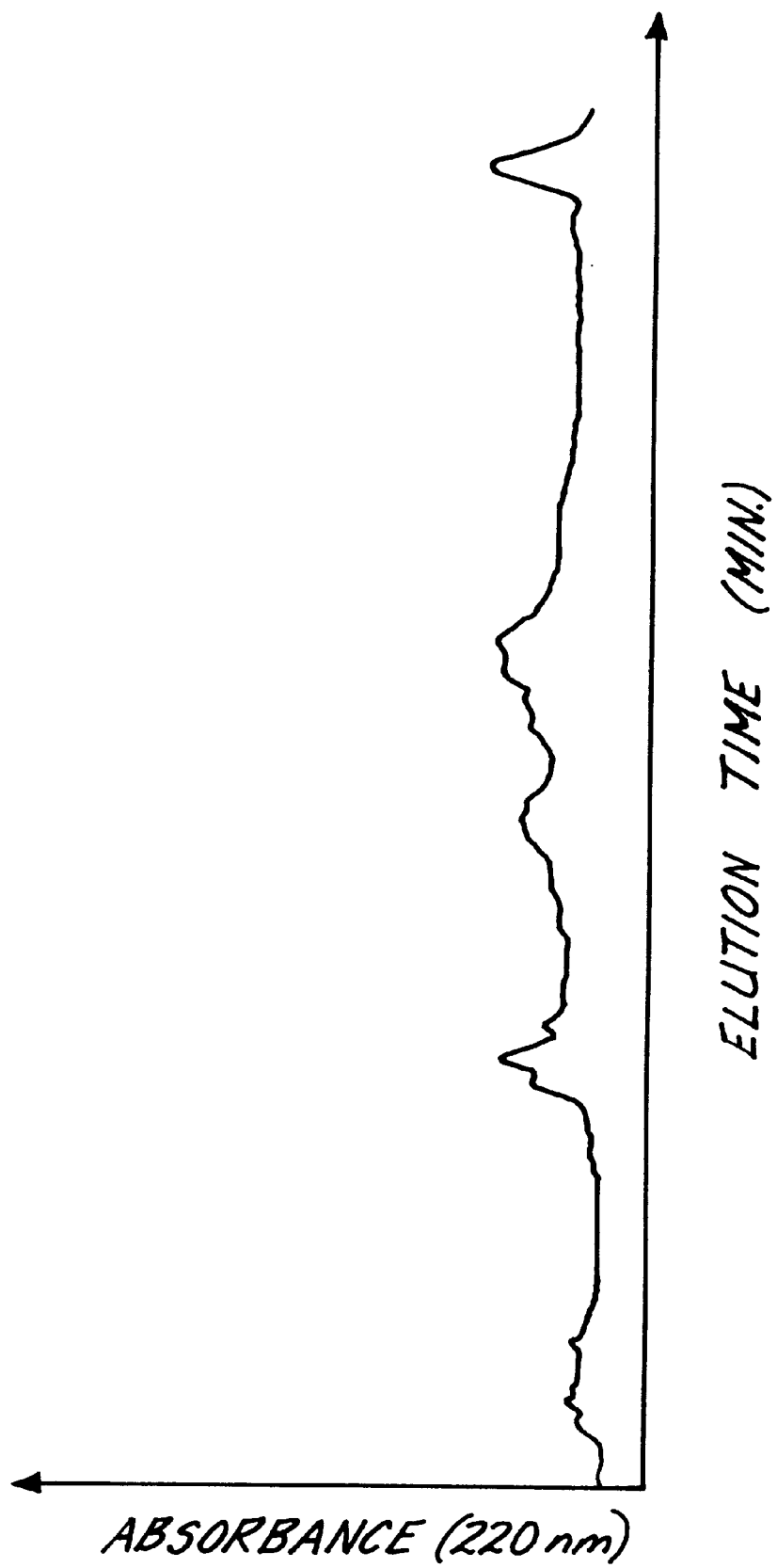
FIG. 3B shows absorbance (220 nm) versus elution time in minutes for the same chromatogram.
Figure 4B:
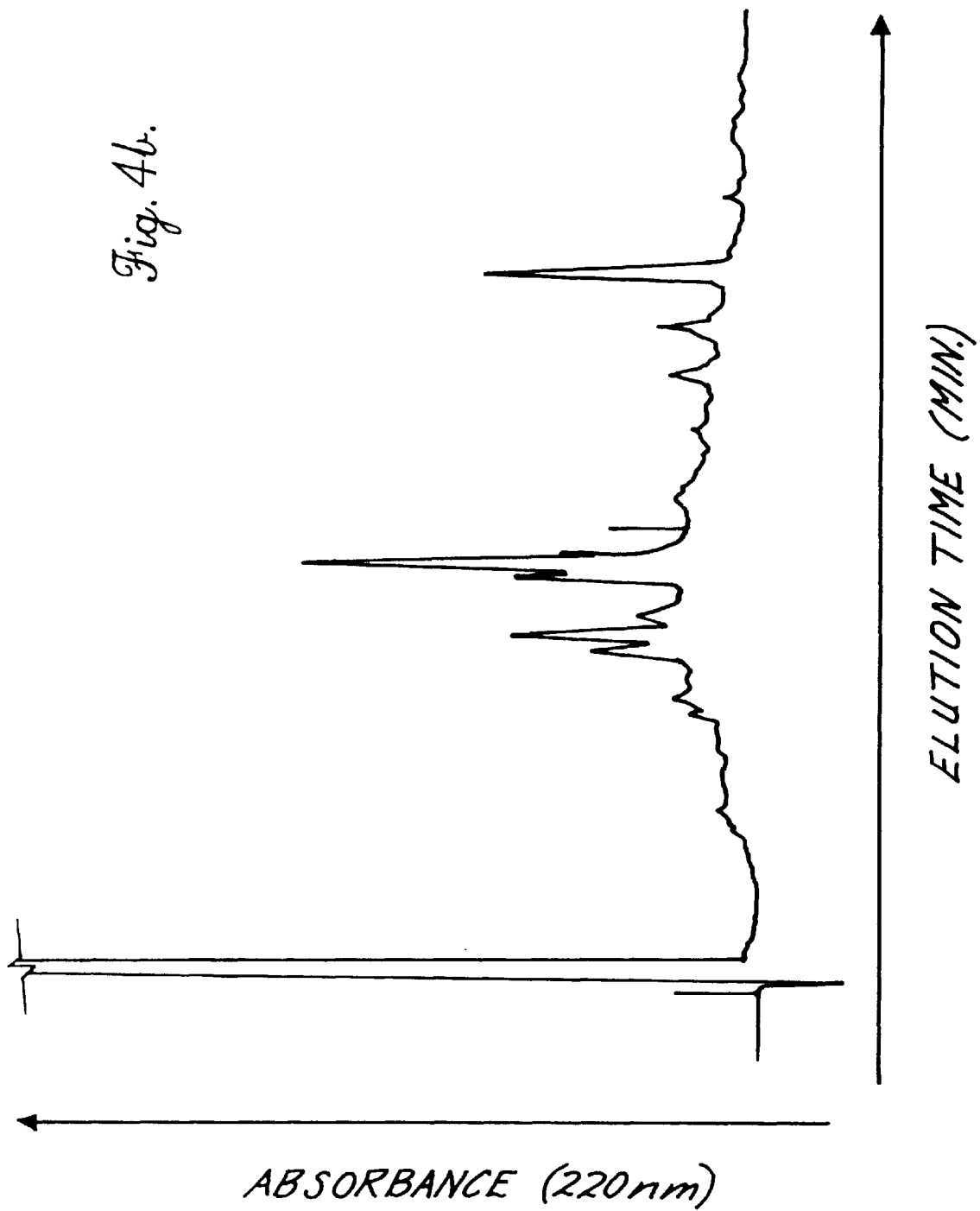
FIG. 4B shows absorbance (220 nm) as a function of elution time during reverse phase HPLC.

FIG. 3A plots relative fluorescence emission at 390 nm (330 nm excitation) versus elution time. The cross-linked collagen type II telopeptides are found primarily in the segment indicated as IV. FIG. 3B plots absorbance at 220 nm as a function of elution time in minutes. Pool IV contains the type II collagen cross-linked peptides. Individual peptides were then resolved from pool IV by reverse phase HPLC on a C-18 column (Aquapore RP-300, 25 cm×4.6 mm, Brownlee Labs), eluting with a gradient of 0–30% (v/v) acetonitrile in 0.1% (v/v) trifluoroacetic acid. FIG. 4A shows a plot of relative fluorescence intensity at 390 nm (297 nm excitation) as a function of elution time. The peaks associated with particular peptides are indicated in FIG. 4A. FIG. 4B shows the relative absorbance at 220 nm as a function of time.

Cross-linked peptide fragments of type III collagen containing HP cross-linking residues may be isolated by a similar combination of steps from the urine of normal growing subjects or, for example, from the urine of patients with inflammatory disorders of the vasculature.

Type I Collagen Telopeptides

This aspect of the invention is based on the discovery that both lysyl pyridinoline (LP) and hydroxylysyl pyridinoline (HP) peptide fragments (i.e., telopeptides, as used herein) derived from reabsorbed bone collagen are excreted in the urine without being metabolized. The invention is also based on the discovery that no other connective tissues contain significant levels of LP and that the ratio of HP to LP in mature bone collagen remains relatively constant over a person's lifetime.

Figure 5:
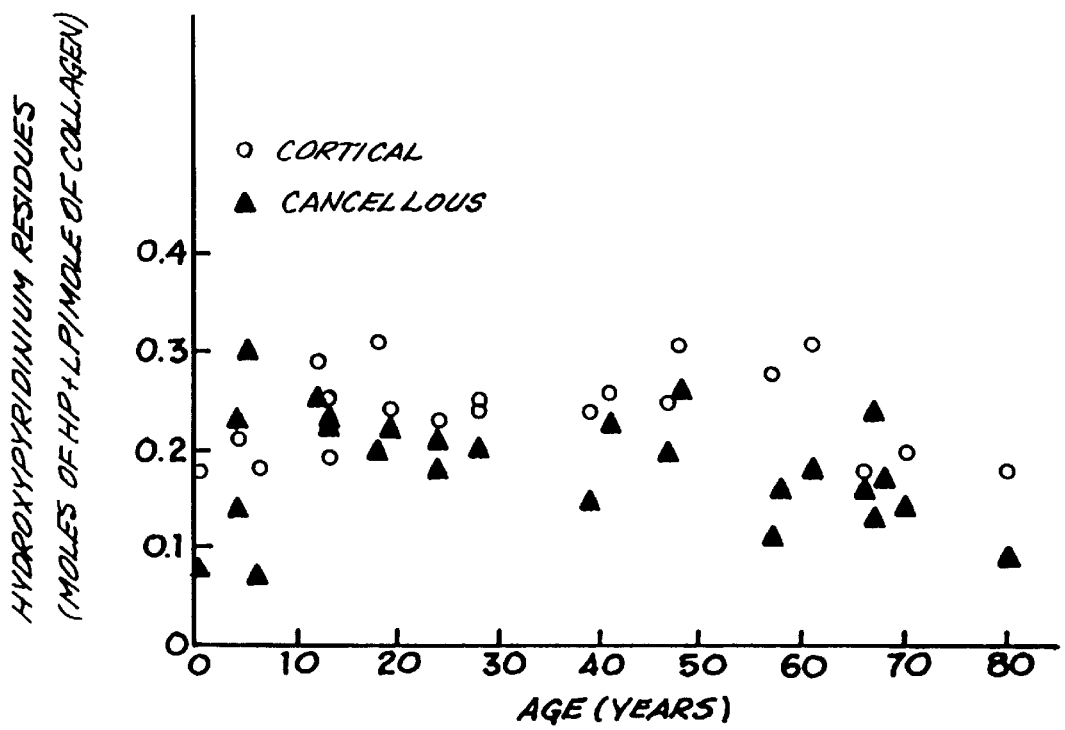
FIG. 5 compares the concentration of HP and LP in both cortical and cancellous human bone with age.
Figure 6:
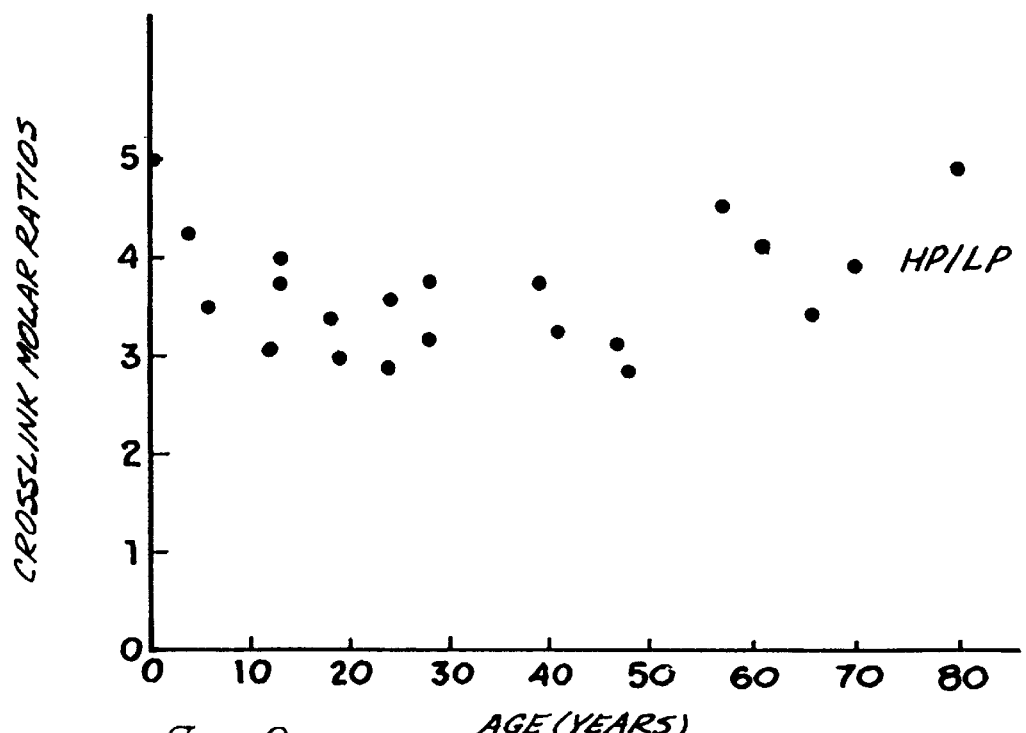
FIG. 6 depicts the cross-link molar ratios of HP to LP as a function of age.

FIG. 5 compares the concentration of HP and LP in both cortical and cancellous human bone with age. It is observed that the concentration of HP plus LP cross-links in bone collagen reaches a maximum by age 10 to 15 years and remains reasonably constant throughout adult life. Furthermore, the ratio of HP to LP, shown in FIG. 6, shows little change throughout life, remaining constant at about 3.5 to 1. These baseline data demonstrate that the 3-hydroxypyridinium cross-links in bone collagen remains relatively constant and therefore that body fluids derived from bone collagen degradation will contain $^3$-hydroxypyridinium cross-linked peptide fragments at concentrations proportional to the absolute rate of bone resorption.

Since LP is the 3-hydroxypyridinium cross-link unique to bone collagen, the method for determining the absolute rate of bone resorption, in its simplest form, is based on quantitating the concentration of peptide fragments containing 3-hydroxypyridinium cross-links and preferably lysyl pyridinoline (LP) cross-links in a body fluid.

As used in this description and in the appended claims with respect to type I, II, or III telopeptides, by "quantitating" is meant measuring by any suitable means, including but not limited to spectrophotometric, gravimetric, volumetric, coulometric, immunometric, potentiometric, or amperometric means the concentration of peptide fragments containing 3-hydroxypyridinium cross-links in an aliquot of a body fluid. Suitable body fluids include urine, serum, and synovial fluid. The preferred body fluid is urine.

Since the concentration of urinary peptides will decrease as the volume of urine increases, it is further preferred that when urine is the body fluid selected, the aliquot assayed be from a combined pool of urine collected over a fixed period of time, for example, 24 hours. In this way, the absolute rate of bone resorption or collagen degradation is calculated for a 24 hour period. Alternatively, urinary peptides may be measured as a ratio relative to a marker substance found in urine such as creatinine. In this way the urinary index of collagen degradation and bone resorption would remain independent of urine volume.

In one embodiment of the present invention, monoclonal or polyclonal antibodies are produced which are specific to the peptide fragments containing lysyl pyridinoline cross-links found in a body fluid such as urine. Type I telopeptide fragments may be isolated from a body fluid of any patient, however, it is preferred that these peptides are isolated from patients with Paget's disease or from rapidly growing adolescents, due to their high concentration of type I peptide fragments. Type II and type III telopeptides may be isolated from a body fluid of any patient but may be more easily obtained from patients suffering from diseases involving type II or type III collagen degradation or from rapidly growing adolescents.

Isolation of Type I Collagen Telopeptides

Urine from patients with active Paget's disease is dialyzed in reduced porosity dialysis tubing (<3,500 mol. wt. cut off Spectropore) at 4° C. for 48 h to remove bulk solutes. Under these conditions the peptides of interest are largely retained. The freeze-dried non-diffusate is then eluted (200 mg aliquots) from a column (90 cm×2.5 cm) of Bio-Gel P2 (200–400 mesh) in 10% acetic acid at room temperature. A region of effluent that combines the cross-linked peptides is defined by measuring the fluorescence of collected fractions at 297 nm excitation/395 nm emission, and this pool is freeze-dried. Further resolution of this material is obtained on a column of Bio-Gel P-4 (200–400 mesh, 90 cm×2.5 cm) eluted in 10% acetic acid.

Two contiguous fraction pools are defined by monitoring the fluorescence of the eluant above. The earlier fraction is enriched in peptide fragments having two amino acid sequences that derive from the C-terminal telopeptide domain of the α1(I) chain of bone type I collagen linked to a third sequence derived from the triple-helical body of bone type I collagen. These three peptide sequences are cross-linked with 3-hydroxypyridinium. The overlapping later fraction is enriched in peptide fragments having an amino acid sequence that is derived from the N-terminal telopeptide domain of bone type I collagen linked through a 3-hydroxy-pyridinium cross-links.

Individual peptides are then resolved from each of the two fractions obtained above by ion-exchange HPLC on a TSK DEAE-5-PW column (Bio Rad 7.5 cm×7.5 mm) eluting with a gradient of NaCl (0–0.2M) in 0.02M Tris-HCI, pH 7.5 containing 10% (v/v) acetonitrile. The N-terminal telopeptide-based and C-terminal telopeptide-based cross-linked peptides elute in a series of 3–4 peaks of fluorescence between 0.08M and 0.15M NaCl. The C-terminal telopeptide-based cross-linked peptides elute first as a series of fluorescent peaks, and the major and minor N-terminal telopeptide-based cross-linked peptides elute towards the end of the gradient as characteristic peaks. Each of these is collected, freeze-dried and chromatographed on a C-18 reverse phase HPLC column (Vydac 218TP54, 25 cm×4.6 mm) eluted with a gradient (0–10%) of acetonitrile: n-propanol (3:1 v/v) in 0.01M trifluoroacetic acid. About 100–500 μg of individual peptide fragments containing 3-hydroxypyridinium cross-links can be isolated by this procedure from a single 24 h collection of Paget's urine.

Amino acid compositions of the major isolated peptides confirmed purity and molecular sizes by the whole number stoichiometry of recovered amino acids. N-terminal sequence analysis by Edman degradation confirmed the basic core structures corresponding to the sequences of the known cross-linking sites in type I collagen and from the matching amino acid compositions. The N-terminal telopeptide sequence of the α2(I) chain was blocked from sequencing analysis due presumably to the known cyclization of the N-terminal glutamine to Pyrrolidone carboxylic acid.

Figure 7A:
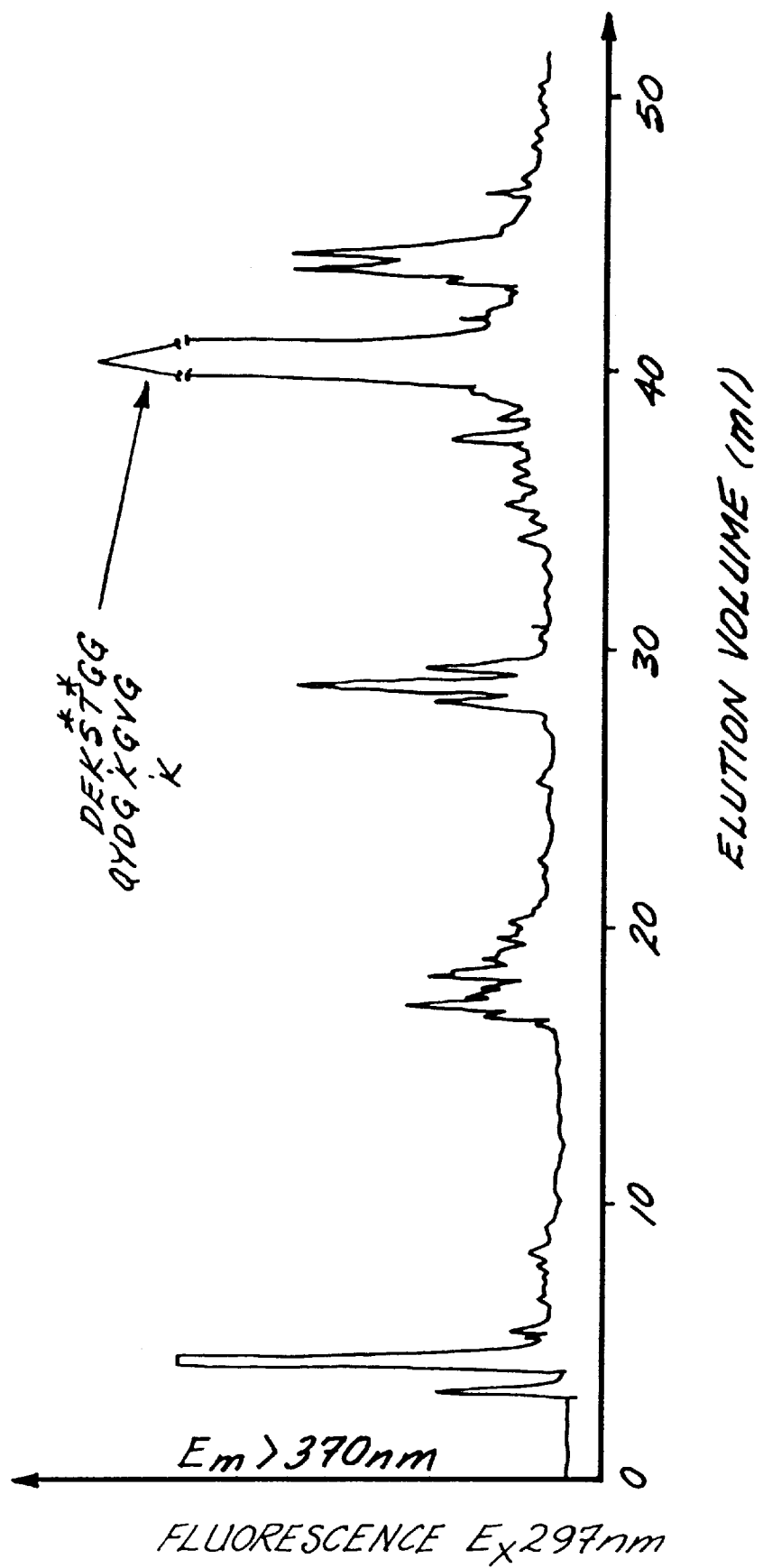
FIG. 7A shows relative fluorescence (297 nm excitation, >370 nm emission) as a function of elution volume during reverse phase HPLC separation of cross-linked type I collagen N-telopeptides.

A typical elution profile of N-terminal telopeptides obtained by the above procedure is shown in FIG. 7A. The major peptide fragment obtained has an amino acid composition: $(Asx)_2(Glx)_2(Gly)_5Val\text{-}Tyr\text{-}Ser\text{-}Thr$, where Asx is the amino acid Asp or Asn and Glx is the amino acid Gln or Glu. The sequence of this peptide is represented by Formula III below.

Figure 7B:
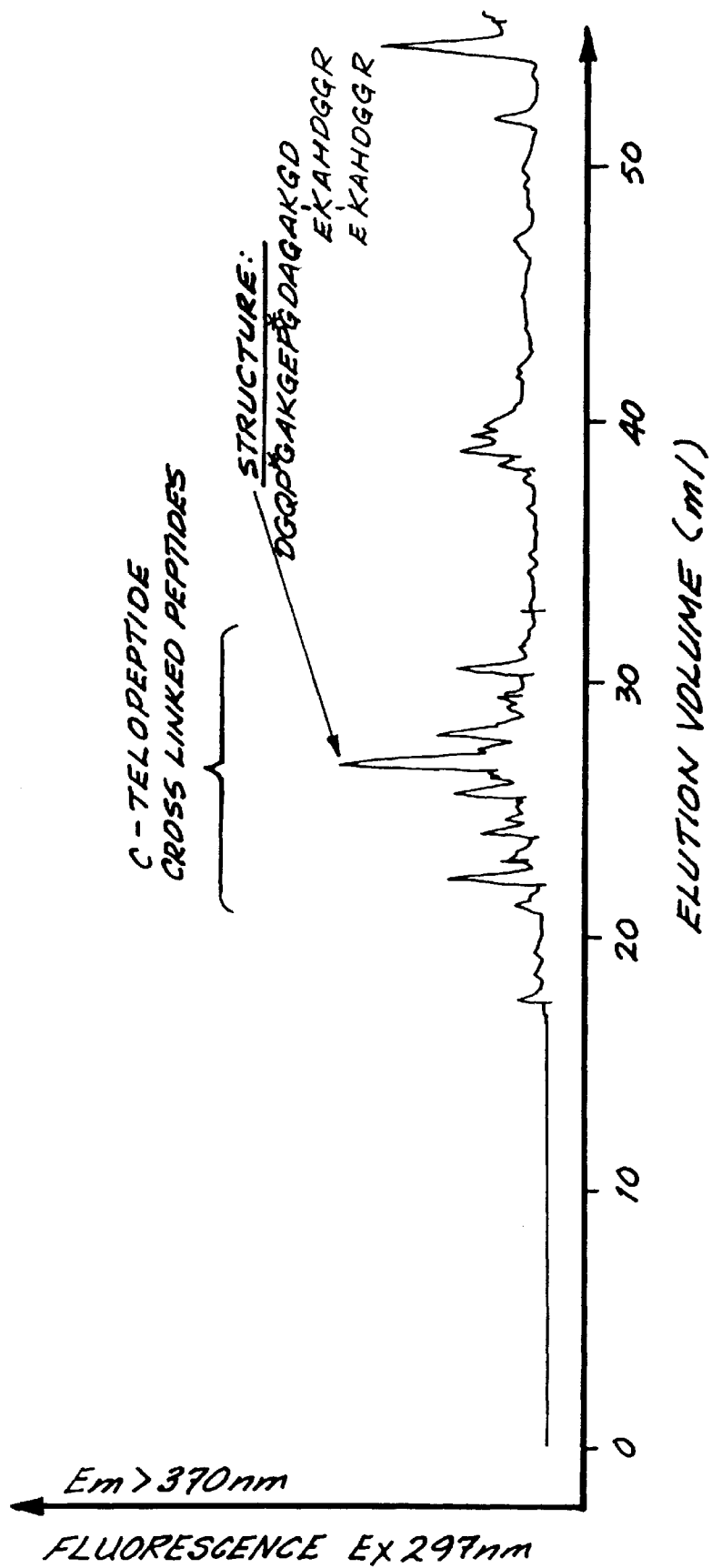
FIG. 7B shows relative fluorescence (297 nm excitation, >370 nm emission) versus elution volume during reverse phase HPLC separation of cross-linked type I collagen C-telopeptides.

The C-terminal telopeptide-based cross-linked peptides resolved by reverse phase HPLC as described above are shown in FIG. 7B. As can be seen from this figure, these peptides are further resolved into a series of C-terminal telopeptides each containing the 3-hydroxypyridinium cross-links. The major peptide, shown in FIG. 7B, was analyzed as described above and was found to have the amino acid composition: $(Asp)_5(Glu)_4(Gly)_{10}(His)_2(Arg)_2(Hyp)_2(Ala)_5$. The sequence of this peptide is represented by formula IV below. It is believed that the other C-terminal telopeptide-based cross-linked peptides appearing as minor peaks in FIG. 7B represent additions and deletions of amino acids to the structure shown in Formula IV. Any of the peptides contained within these minor peaks are suitable for use as immunogens as described below.

FORMULA III

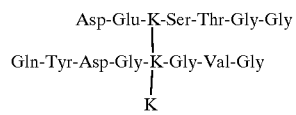

FORMULA IV

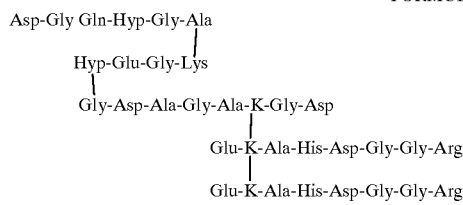

FORMULA V

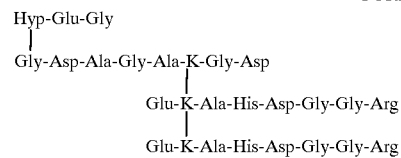

and

FORMULA VI

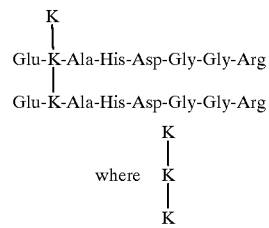

represents the HP or LP cross-links and Gln represents glutamine or pyrrolidone carboxylic acid.

Equivalents of the peptides represented by the above structures, in terms of their presence in a body fluid due to collagen degradation, include those cases where there is some variation in the peptide structure. Examples of such variation include 1–3 amino acid additions to the N and C termini as well as 1–3 terminal amino acid deletions. For example, a peptide corresponding to Formula III, but having a tyrosine residue attached to the amino terminus of the N-terminal aspartate residue has been detected in relatively minor quantities in human urine. Smaller peptide fragments of the molecule represented by Formula IV derived from bone resorption are especially evident in urine. These are found in the minor peaks of the C-terminal telopeptide fraction seen in FIG. 7B and can be identified by amino acid composition and sequence analysis.

Examples of Procedures for Quantitating Peptides

A. Immunological Procedure For Quantitating Peptides

Immunological binding partners capable of specifically binding to peptide fragments derived from bone collagen obtained from a physiological fluid can be prepared by methods well known in the art. The preferred method for isolating these peptide fragments is described above. By immunological binding partners as used herein is meant antibodies and antibody fragments capable of binding to a telopeptide.

Both monoclonal and polyclonal antibodies specifically binding the peptides disclosed herein and their equivalents are prepared by methods known in the art. For example, Campbell, A. M. *Laboratory Techniques in Biochemistry and Molecular Biology*, Vol. 13 (1986). Elsevier, herein incorporated by reference. It is possible to produce antibodies to the above peptides or their equivalents as isolated. However, because the molecular weights of these peptide fragments are generally less than 5,000, it is preferred that the hapten be conjugated to a carrier molecule. Suitable carrier molecules include, but are not limited to, bovine serum albumin, ovalbumin, thyroglobulin, and keyhole limpet hemocyanin (KLH). Preferred carriers are thyroglobulin and KLH.

It is well known in the art that the orientation of the hapten, as it is bound to the carrier protein, is of critical importance to the specificity of the anti-serum. Furthermore, not all hapten-protein conjugates are equally successful immunogens. The selection of a protocol for binding the particular hapten to the carrier protein therefore depends on the amino acid sequence of the urinary peptide fragments selected. For example, if the peptide represented by Formula III Is selected, a preferred protocol involves coupling this hapten to keyhole limpet hemocyanin (KLH), or other suitable carrier, with glutaraldehyde. An alternative protocol is to couple the peptides to KLH with a carbodiimide. These protocols help to ensure that the preferred epitope (discussed below under the heading "Characteristics of a Preferred Epitope)" are presented to the primed vertebrate antibody producing cells (e.g., B lymphocytes).

Other peptides, depending on the source, may require different binding protocols. Accordingly, a number of binding agents may be suitably employed. These include, but are not limited to, carbodiimides, glutaraldehyde, mixed anhydrides, as well as both homobifunctional and heterobifunctional reagents (see for example the Pierce 1986–87 catalog, Pierce Chemical Co., Rockford, Ill.). Preferred binding agents include carbodiimides and heterobifunctional reagents such as m-Maleimidobenzyl-N-hydroxysuccinimide ester (MBS).

Methods for binding the hapten to the carrier molecule are known in the art. See for example, Chard, T., *Laboratory Techniques in Biochemistry and Molecular Biology*, Vol. 6 (1987) Partz Elsevier, N.Y., herein incorporated by reference.

Either monoclonal or polyclonal antibodies to the hapten-carrier molecule immunogen can be produced. However, it is preferred that monoclonal antibodies (MAb) be prepared. For this reason it is preferred that immunization be carried out in the mouse. Immunization protocols for the mouse usually include an adjuvant. Examples of suitable protocols are described by Chard, T. (1987) vida supra. Spleen cells from the immunized mouse are harvested and homogenized and thereafter fused with cancer cells in the presence of polyethylene glycol to produce a fused cell hybrid which produces monoclonal antibodies specific to peptide fragments derived from collagen. Examples of such peptides are represented by the formulas given above. Suitable cancer cells include myeloma, hepatoma, carcinoma, and sarcoma cells. Detailed descriptions of this procedure, including screening protocols, protocols for growing selected hybrid cells and harvesting monoclonal antibodies produced by the selected hybrid cells are provided in Galfre, G. and Milstein, C., *Meth. Enzymol.*, 73:1 (1981). A preferred preliminary screening protocol involves the use of peptide fragments derived from bone collagen resorption and containing 3-hydroxypyridinium cross-links in a solid phase radioimmunoassay. A specific example describing a preferred monoclonal antibody is provided below.

The monoclonal antibodies or other immunological binding partners used in connection with the present are preferably specific for a particular type of collagen telopeptide. For example, assays for the type II or type III collagen degradation telopeptides should preferably be able to distinguish between the type I, type II, and type III peptides. However, in some cases, such selectivity will not be necessary, for example, if it is known that a patient is not suffering degradation of one type of collagen but is suspected of suffering degradation from the assayed type of collagen. Because of the differences in amino acid sequences between the type I, type II, and type III families of telopeptides, cross-reactivity should not occur to a significant degree. Indeed, hybridomas can be selected for during the screening of splenocyte fusion clones that produce monoclonal antibodies specific for the cross-linked telopeptide of interest (and lack affinity for those of the other two collagen types). Based on the differences in sequence of the isolated peptide structures, such specificity is entirely feasible. Peptide fragments of the parent types I, II and III collagens, suitable for such hybridoma screening, can be prepared from human bone, cartilage and other tissues and used to screen clones from mice immunized appropriately with the individual cross-linked peptide antigens isolated from body fluid.

Immunological binding partners, especially monoclonal antibodies, produced by the above procedures, or equivalent procedures, are employed in various immunometric assays to quantitate the concentration of the peptides having 3-hydroxypyridinium cross-links described above. These immunometrie assays preferably comprise a monoclonal antibody or antibody fragment coupled to a detectable marker. Examples of suitable detectable markers include but are not limited to: enzymes, coenzymes, enzyme inhibitors, chromophores, fluorophores, chemiluminescent materials, paramagnetic metals, spin labels, and radionuclides. Examples of standard immunometric methods suitable for quantitating the telopeptides include, but are not limited to, enzyme linked imimunosorbent assay (ELISA) (Ingvall, E., *Meth. Enzymol.*, 70 (1981)), radio-immunoassay (RIA), and "sandwich" immunoradiometric assay (IRMA).

In its simplest form, these immunometric methods can be used to determine the absolute rate of bone resorption or collagen degradation by simply contacting a body fluid with the immunological binding partner specific to a collagen telopeptide having a 3-hydroxypyridinium cross-link.

It is preferred that the immunometric assays described above be conducted directly on untreated body fluids (e.g. urine, blood, serum, or synovial fluid). Occasionally, however, contaminating substances may interfere with the assay necessitating partial purification of the body fluid. Partial purification procedures include, but are not limited to, cartridge adsorption and elution, molecular sieve chromatography, dialysis, ion exchange, alumina chromatography, hydroxyapatite chromatography and combinations thereof.

Test kits, suitable for use in accordance with the present invention, contain specific binding partners such as monoclonal antibodies prepared as described above, that specifically bind to peptide fragments derived from collagen degradation found in a body fluid. It is preferred that the specific binding partners of this test kit be coupled to a detectable marker of the type described above. Test kits containing a panel of two or more specific binding partners, particularly immunological binding partners, are also contemplated. Each immunological binding partner in such a test kit will preferably not cross-react substantially with a telopeptide derived from another type of collagen. For example, an immunological binding partner that binds specifically with a type II collagen telopeptide should preferably not cross-react with either a type I or type III collagen telopeptide. A small degree (e.g., 5–10%) of cross-reactivity may be tolerable. Other test kits may contain a first specific binding partner to a collagen-derived telopeptide having a cross-link containing a pyridinium ring (which may be OH-substituted), and a second specific binding partner to a telopeptide having the same structure as the first telopeptide except that the pyridinium ring has been cleaved, such as photolytically.

(i) Monoclonal Antibody Production

The following is an example of preparation of a monoclonal antibody against a peptide immunogen based on Formula III above.

A fraction enriched in the peptide of Formula III (indicative of bone collagen degradation) was prepared from adolescent human urine using reverse phase and molecular sieve chromatography. The peptide was conjugated to keyhole limpet hemocyanin (KLH) with glutaraldehyde using standard procedures. Mice (Balb/c) were immunized subcutaneously with this conjugate (50–70 $\mu$g), first in complete Freund's adjuvant, then boosted (25 $\mu$g) at 3 weekly intervals in incomplete Freund's adjuvant intraperitoneally. After test bleeds had shown a high titer against the Formula III peptide (referred to herein as P1) conjugated to bovine serum albumin (BSA) using an ELISA format, selected mice were boosted with a low dose (5 $\mu$g) of the immunogen in sterile PBS intravenously. Three days later, cells from the spleens of individual mice were fused with mouse myeloma cells using standard hybridoma technology. The supernatants of hybridoma clones growing in individual wells of 96-well plates were screened for reactive monoclonal antibodies, initially using a crude P1 preparation conjugated to BSA. After formal cloning by limiting dilution, the antibodies produced by individual hybridomas were characterized against a panel of screening antigens using ELISA analysis. These antigens were the P1 (Formula III) and P2 (Formula VII) peptides conjugated to BSA. An inhibition assay was used in which P1 conjugated to BSA was plated out in the plastic wells, and antibody was pre-incubated with a solution of the potential antigen. A secondary antibody (goat anti-mouse IgG conjugated to horseradish peroxidase, HRP) was used for color development using an appropriate substrate. A desirable monoclonal antibody with high binding affinity for the P1 peptide was identified. When used as an ascites fluid preparation, the antibody worked in an inhibition assay with optimal color yield at 2 million-fold dilution (which indicates a binding constant in the range of $10^{-9}$ to $10^{-11}$ $M^{-1}$, most likely about $10^{-10}$ $M^{-1}$). In an ELISA format, the antibody was able to detect and measure P1 present in normal human urine without any concentration or clean-up steps. The hybridoma that produces this preferred monoclonal antibody has been deposited at the American Type Culture Collection (ATCC), 12301 Parklawn Drive, Rockville, Md. 20852, under accession number HB10611 on Nov. 20, 1990. This hybridoma is designated below as 1H11; the monoclonal antibody it produces is designated below as MAb-1H11.

Sandwich assays were also shown to work using the P1-specific monoclonal antibody and a polyclonal antiserum raised in rabbits against conjugated P1. Either P1-specific monoclonal antibodies, polyclonal antiserum, binding fragments thereof, or the like can be used to bind specifically to P1 from urine, in a detectable manner using standard ELISA and other immunoassay protocols.

(ii) Characteristics of a Preferred Epitope

Figures 9, 10:
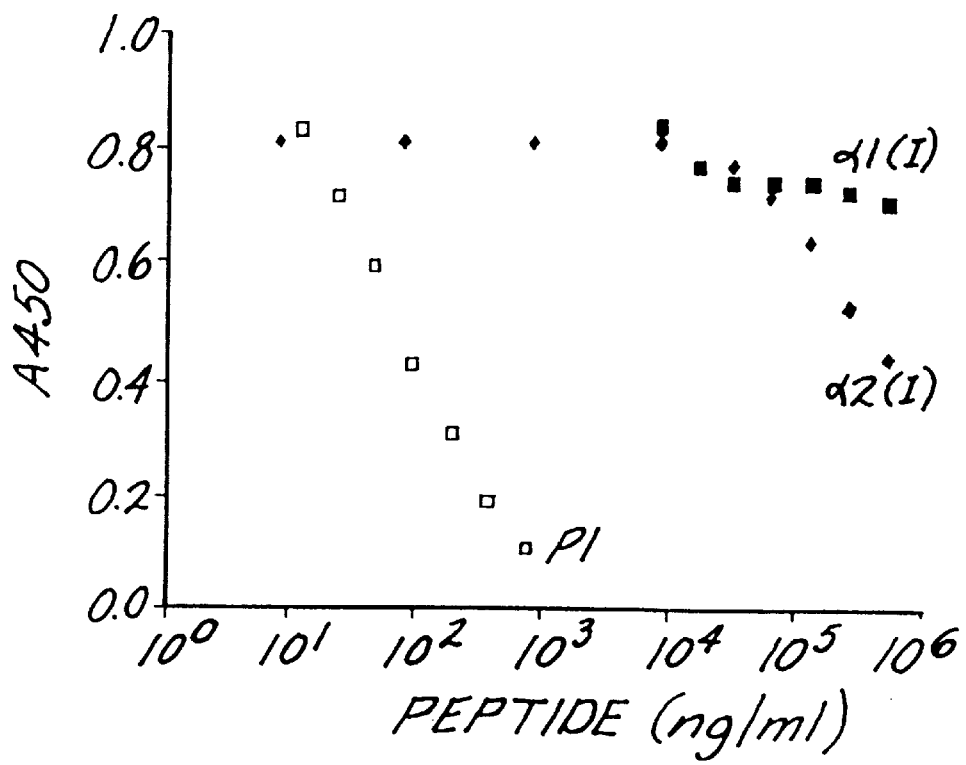
FIG. 9 shows results of binding experiments with the representative monoclonal antibody HB 10611 and: the P1 peptide (Formula III herein, open squares); an α2 (I) N-telopeptide (Gln-Tyr-Asp-Gly-Lys-Gly-Val-Gly-Cys (SEQ ID NO:1), solid diamonds); and an α1 (I) N-telopeptide (Tyr-Asp-Glu-Lys-Ser-Thr-Gly-Gly-cys (SEQ ID NO:2), solid squares).
FIG. 10 shows a portion of the structure of the N-telopeptide region of decalcified human bone collagen. The P1 peptide (Formula III) is enclosed in a box; it contains an epitope that correlates with bone resorption.

The epitope recognized by the antibody MAb-1H11 is embodied in the structure of P1. The epitope is recognized in pure P1 and in certain larger peptides that contained the P1 structure (e.g., P1 attached to a tyrosine residue via the N-terminal aspartate residue of P1). The epitope includes chemical features of both of the two telopeptide sequences embodied in the structure of peptide P1. Peptides synthesized to match the human $\alpha$1 (I) and $\alpha$2 (I) N-telopeptide sequences, with the addition of a C-terminal cysteine for coupling to bovine serum albumin (i.e., Tyr-Asp-Glu-Lys-Ser-Thr-Gly-Gly-Cys (SEQ ID NO:2) and Gln-Tyr-Asp-Gly-Lys-Gly-Val-Gly-Cys (SEQ ID NO:1)), were not recognized by MAb-1H11. This was shown by ELISA using the free peptides competing against plated-out P1 (see FIG. 9) or directly as binding partners conjugated to BSA and plated out. Referring to FIG. 9, the absorbance at $\lambda$=450 nm of a detectable marker is plotted against the concentration of free P1 peptide. As the amount of free P1 increases, the amount of detectable marker bound to immobilized (plated-out) P1 diminishes. In comparison, the $\alpha$2 (I) and $\alpha$1 (I) N-telopeptides demonstrate little if any significant competitive binding with MAb-1H11.

In addition, a larger form of P1 bearing a tyrosine residue on the N-terminal aspartic acid was recovered from urine by affinity binding to MAb-1H11, but in lower yield than P1. Other slightly larger peptides bearing the P1 epitope were also recovered but in even smaller amounts.

The antibody was not selective for the nature of the cross-link in P1, i.e., whether hydroxylysyl pyridinoline (HP) or lysyl pyridinoline (LP). Both HP-containing and LP-containing forms were bound, apparently with equal affinity, judging by the analysis of peptides isolated from urine by an affinity column consisting of MAb-1H11 coupled to agarose.

The free cross-linking amino acids, HP and LP, either made by acid hydrolysis from bone collagen or as present naturally in urine were not recognized by MAb-1H11. After photolytic opening of the 3-pyridinol ring in peptide P1 with UV light (long UV wavelengths), specific antibody binding was also unaffected, presumably because the individual peptides remained cross-linked to each other. The epitope recognized by MAb-1H11, therefore, is made up of at least a combination of chemical and conformational features embodied in the two telopeptide sequences shown boxed in FIG. 10, together with steric features imposed by the trivalent cross-linking amino acid that links them. The $\alpha$2 (I) N telopeptide sequence, Gln-Tyr-Asp-Gly-Lys (SEQ ID NO:3), is a particularly significant part of the epitope.

The fact that the epitope recognized by MAb-1H11 does not depend on an intact pyridinium ring is an unexpected discovery. If ring-opening occurs either in vivo or even in vitro under routine handling conditions, as appears likely, then a quantitative assay of the subject peptide(s) having intact pyridinium rings will underestimate the amount of bone resorption. Preliminary observations indicate that degradation of pyridinium rings in the subject peptides appears to occur particularly in urine and/or in urine samples, even if refrigerated. Accordingly, an assay based on the present disclosure is expected to be comparatively more accurate. Two embodiments are envisioned: a single specific binding partner is employed that recognizes both closed and open-ringed embodiments of the targeted peptide(s); or two specific binding partners are employed, which differentiate between the closed- and open-ringed epitopes, respectively.

Further experiments showed that the epitope resides in human bone collagen but is exposed and bound by MAb-1H11 only after extensive proteolysis. Thus, peptides produced from decalcified human bone collagen by bacterial collagenase were bound by MAb-1H11 and shown to be derived from the N-telopeptide to helix site shown in FIG. 10. One form contained the hexapeptide Gly-Ile-Lys-Gly- His-Arg (SEQ ID NO:4) (in place of the non-telopeptide K arm in P1), which is clearly derived from α1 (I) residues 928–933. Another form embodied an equivalent but distinct hexapeptide that was derived from the α2 (I) chain. Fragments of human bone collagen solubilized by pepsin, CNBr, or trypsin were not recognized by MAb-1H11, either in an ELISA format when used as competitive inhibitors or on a Western blot after SDA-polyacrylamide electrophoresis, indicating that these solubilizing agents do not produce the epitope recognized by MAb-1H11.

B. Electrochemical Procedure For Assaying For Peptides

An alternative procedure for assaying for the above-described peptides consists of measuring a physical property of the peptides having 3-hydroxypyridinium cross-links. One such physical property relies upon electrochemical detection. This method consists of injecting an aliquot of a body fluid, such as urine, into an electrochemical detector poised at a redox potential suitable for detection of peptides containing the 3-hydroxypyridinium ring. The 3-hydroxypyridinium ring, being aphenol, is subject to reversible oxidation and therefore the electrochemical detector (e.g., Model 5100A Coulochem sold by Esa 45 Wiggins Ave., Bedford, Mass.) is a highly desirable instrument suitable for quantitating the concentration of the present peptides. Two basic forms of electrochemical detector are currently commercially available: amperometric (e.g., Bio-Analytical Systems) and coulometric (ESA, Inc., Bedford, Mass. 01730). Both are suitable for use in accordance with the present invention, however, the latter system is inherently more sensitive and therefore preferred since complete oxidation or reduction of the analyzed molecule in the column effluent is achieved. In addition, screening or guard electrodes can be placed "upstream" from the analytical electrode to selectively oxidize or reduce interfering substances thereby greatly improving selectivity. Essentially, the voltage of the analytical electrode is tuned to the redox potential of the sample molecule, and one or more pretreatment cells are set to destroy interferents in the sample.

In a preferred assay method, a standard current/voltage curve is established for standard peptides containing lysyl pyridinoline or hydroxylysyl pyridinoline in order to determine the proper voltage to set for optimal sensitivity. This voltage is then modified depending upon the body fluid, to minimize interference from contaminants and optimize sensitivity. Electrochemical detectors, and the optimum conditions for their use are known to those skilled in the art. Complex mixtures of body fluids can often be directly analyzed with the electrochemical detector without interference. Accordingly, for most patients no pretreatment of the body fluid is necessary. In some cases however, interfering compounds may reduce the reliability of the measurements. In such cases, pretreatment of the body fluid (e.g., urine) may be necessary.

Accordingly, in an alternative embodiment of the invention, a body fluid is first purified prior to electrochemically titrating the purified peptide fragments. The purification step may be conducted in a variety of ways including but not limited to dialysis, ion exchange chromatography, alumina chromatography, hydroxyapatite chromatography, molecular sieve chromatography, or combinations thereof. In a preferred purification protocol, a measured aliquot (25 ml) of a 24 hour urine, sample is dialyzed in reduced porosity dialysis tubing to remove the bulk of contaminating fluorescent solutes. The non-diffusate is then lyophilized, redissolved in 1% heptafluorobutyric acid (HFBA), an ion pairing solution, and the peptides adsorbed on a Waters Sep-Pak C-18 cartridge. This cartridge is then washed with 5 ml of 1% HFBA, and then eluted with 3 ml of 50% methanol in 1% HFBA.

Another preferred method of purification consists of adsorbing a measured aliquot of urine onto an ion-exchange adsorption filter and eluting the adsorption filter with a buffered eluting solution. The eluate fractions containing peptide fragments having 3-hydroxypyridinium cross-links are then collected to be assayed.

Still another preferred method of purification employs molecular sieve chromatography. For example, an aliquot of urine is applied to a Bio-Gel P2 or Sephadex G-20 column and the fraction eluting in the 1000–5000 Dalton range is collected. It will be obvious to those skilled in the art that a combination of the above methods may be used to purify or partially purify urine or other body fluids in order to isolate the peptide fragments having 3-hydroxypyridinium cross-links. The purified or partially purified peptide fragments obtained by the above procedures may be subjected to additional purification procedures, further processed or assayed directly in the partially purified state. Additional purification procedures include resolving partially purified peptide fragments employing high performance liquid chromatography (HPLC) or microbore HPLC when increased sensitivity is desired. These peptides may then be quantitated by electrochemical titration.

A preferred electrochemical titration protocol consists of tuning the redox potential of the detecting cell of the electrochemical detector (Coulochem Model 5100A) for maximum signal with pure HP. The detector is then used to monitor the effluent from a C-18 HPLC column used to resolve the partially purified peptides.

C. Fluorometric Procedure For Quantitating Peptides

An alternative preferred method for quantitating the concentration of peptides having 3-hydroxypyridinium cross-links as described herein is to measure the characteristic natural fluorescence of these peptides. For those body fluids containing few naturally occurring fluorescent materials other than the 3-hydroxypyridinium cross-links, fluorometric assay may be conducted directly without further purification of the body fluid. In this case, the peptides are resolved by HPLC and the natural fluorescence of the HP and LP amino acid residues is measured at 395 nm upon excitation at 297 nm, essentially as described by Eyre, D. R., et al., *Analyte. Biochem.* 137:380 (1984), herein incorporated by reference.

It is preferred, in accordance with the present invention, that the fluorometric assay be conducted on urine. Urine, however, usually contains substantial amounts of naturally occurring fluorescent contaminants that must be removed prior to conducting the fluorometric assay. Accordingly, urine samples are first partially purified as described above for electrochemical detection. This partially purified urine sample can then be fluorometrically assayed as described above. Alternatively, the HP and LP cross-linked peptides in the partially purified urine samples or other body fluids can be hydrolyzed in 6M HCI at about 108° C. for approximately 24 hours as described by Eyre, et al. (1984) vida supra. This process hydrolyzes the amino acids connected to the lysine pirecursors of "tripeptide" HP and LP cross-links, producing the free HP and LP amino acids represented by Formulae I and II. These small "tripeptides" are then resolved by the techniques described above, preferably by HPLC, and the natural fluorescence is measured (Ex 297 nm, Ex 390 nm)., Optionally, the body fluid (preferably urine) is passed directly through a C-18 reverse phase affinity cartridge after adding acetonitrile/methanol 5 to 10% V/V. The non-retentate is adjusted to 0.05–0.10M with a cationic ion-pairing agent such as tetrabutyl ammonium hydroxide and passed through a second C-18 reverse phase cartridge. The washed retentate, containing fluorescent peptides, from this second cartridge is eluted with acetonitrile:water (or methanol:water), dried and fluorescent peptides are analyzed by reverse phase HPLC or microbore HPLC using an anionic ion-pairing agent such as 0.01M trifluoroacetic acid in the eluant.

Figure 8B:
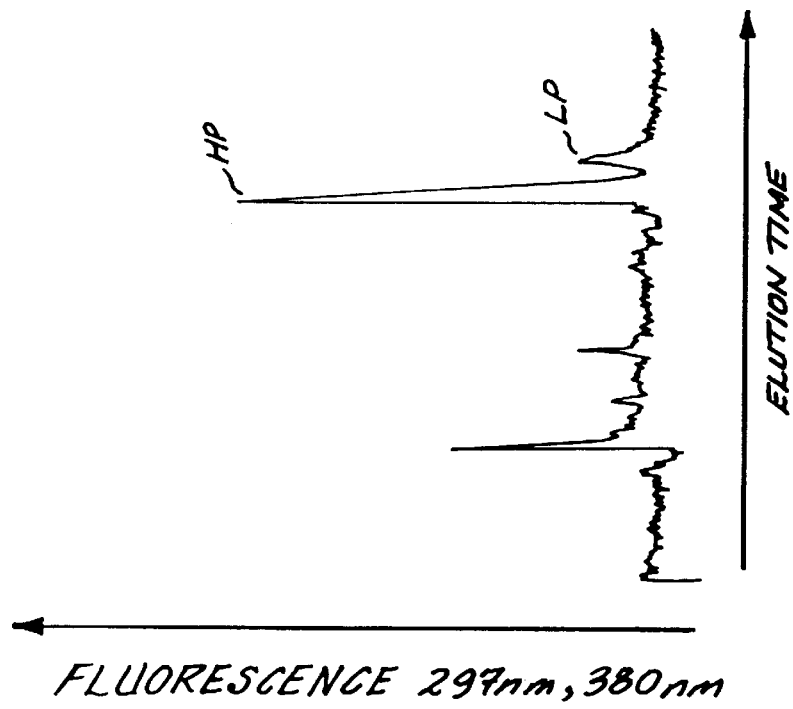
FIG. 8B shows relative fluorescence (297 nm excitation, >380nm emission) as a function of elution time for the cross-linked type I collagen telopeptides.
Figure 8A:
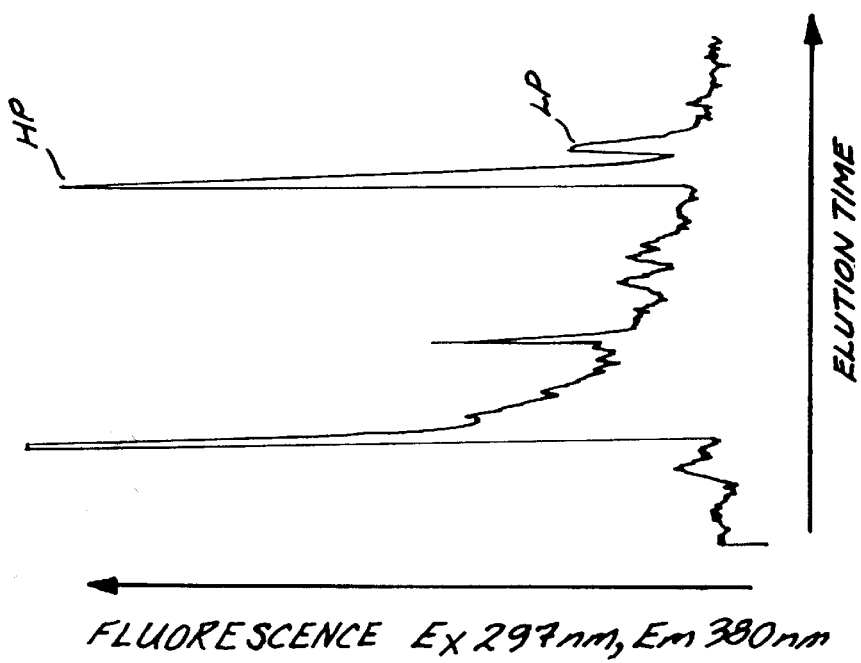
FIG. 8A shows relative fluorescence (297 nm excitation, >380 nm emission) as a function of elution time for the cross-linked type I collagen telopeptides.

FIG. 8A displays the elution profile resolved by reverse phase HPLC of natural fluorescence for a hydrolysate of peptide fragments from normal human urine. Measurement of the integrated area within the envelope of a given component is used to determine the concentration of that component within the sample. The ratio of HP:LP found in normal human urine and urine from patients having Paget's disease, FIG. 8B, are both approximately 4.5:1. This is slightly higher than the 4:1 ratio found in bone itself (Eyre, et al., 1984). The higher ratio found in urine indicates that a portion of the HP fraction in urine may come from sources other than bone, such as the diet, or other sources of collagen degradation, i.e., cartilage catabolism. It is for this reason that it is preferred that LP which derives only from bone be used to provide an absolute index of bone resorption. However, in the absence of excessive cartilage degradation such as in rheumatoid arthritis or in cases where bone is rapidly being absorbed, HP or a combination of HP plus LP may be used as an index of bone resorption.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

What is claimed is:

1. A synthetic linear peptide

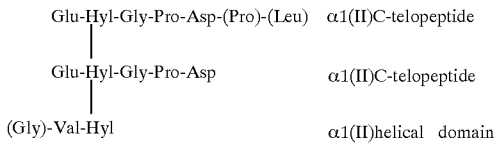

selected from among the group consisting of Glu-Lys-Gly-Pro-Asp (SEQ ID NO:5), Glu-Lys-Gly-Pro-Asp-Pro (SEQ ID NO:6), and Glu-Lys-Gly-Pro-Asp-Pro-Leu (SEQ ID NO:7).

2. A synthetic peptide of claim 1, consisting of Glu-Lys-Gly-Pro-Asp (SEQ ID NO:5).

3. A synthetic peptide of claim 1, consisting of Glu-Lys-Gly-Pro-Asp-Pro (SEQ ID NO:6).

4. A synthetic peptide of claim 1, consisting of (Glu-Lys-Gly-Pro-Asp-Pro-Leu (SEQ ID NO:7).

5. A synthetic linear peptide consisting essentially of the amino acid sequence of an α1(II) carboxy-telopeptide component chain of a cross-linked telopeptide degradation product of type II collagen, wherein the cross-linked telopeptide degradation product of type II collagen is isolatable from a urine sample of a growing adolescent by a process which comprises the following steps:

passing the urine sample through a hydrophobic interaction support, eluting retained peptides, passing the eluant through an ion-exchange support, eluting retained peptides, and drying the eluted peptides, fractionating the dried material by molecular sieve chromatography on a polyacrylamide gel column eluted by 10% (v/v) acetic acid, identifying fractions of effluent that contain 3-hydroxypyridinium cross-linked peptides by measuring the fluorescence of collected fractions at 297 nm excitation/390 nm emission, and freeze-drying fluorescent fractions, fractionating the dried material by ion-exchange chromatography on a DEAE-HPLC column eluted with a gradient of NaCl (0–0.5M) in 0.02M Tris-HCl, ph 7.5 containing 10% (v/v) acetonitrile, identifying fractions that contain 3-hydroxypyridinium cross-linked peptides by fluorescence as measured above, and freeze-drying fluorescent fractions, fractionating the dried material by reverse phase HPLC on a C-18 column eluted with a gradient of 0–30% (v/v) acetonitrile in 0.1% (v/v) tritluoroacetic acid, and isolating peaks associated with individual peptides by fluorescence as measured above, selecting by amino acid analysis an isolated peak associated with a carboxy-terminal telopeptide degradation product of type II collagen that contains a 3-hydroxypyridinium cross-link, and determining the amino acid sequence of an α1 (II) carboxy-telopeptide component chain of the selected cross-linked carboxy-telopeptide degradation product of type II collagen; and wherein the amino acid residue in the synthetic linear peptide corresponding in position to the 3-hydroxypyridinium cross-link in the α1 (II) carboxy-telopeptidc component chain of the selected degradation product is lysine.

* * * * *